US011518998B2

(12) United States Patent
Hamada et al.

(10) Patent No.: US 11,518,998 B2
(45) Date of Patent: Dec. 6, 2022

(54) METHOD FOR CREATING TRANSFORMED PLANT

(71) Applicant: KANEKA CORPORATION, Osaka (JP)

(72) Inventors: Haruyasu Hamada, Hyogo (JP); Yozo Nagira, Hyogo (JP); Ryuji Miki, Hyogo (JP); Naoaki Taoka, Hyogo (JP); Ryozo Imai, Hokkaido (JP)

(73) Assignee: KANEKA CORPORATION, Osaka (JP)

( * ) Notice: Subject to any disclaimer, the term of this patent is extended or adjusted under 35 U.S.C. 154(b) by 150 days.

(21) Appl. No.: 16/189,442

(22) Filed: Nov. 13, 2018

(65) Prior Publication Data

US 2019/0062766 A1    Feb. 28, 2019

Related U.S. Application Data

(63) Continuation of application No. PCT/JP2017/018262, filed on May 15, 2017.

(30) Foreign Application Priority Data

May 13, 2016  (JP) ............................. JP2016-097464

(51) Int. Cl.
| | | |
|---|---|---|
| C12N 15/82 | (2006.01) |
| C12N 15/09 | (2006.01) |
| A01H 1/00 | (2006.01) |
| A01H 1/06 | (2006.01) |
| A01H 5/10 | (2018.01) |

(52) U.S. Cl.
CPC ........... *C12N 15/8207* (2013.01); *A01H 1/00* (2013.01); *A01H 1/06* (2013.01); *A01H 5/10* (2013.01); *C12N 15/09* (2013.01); *C12N 15/8226* (2013.01); *C12N 15/8227* (2013.01); *C12N 15/8234* (2013.01)

(58) Field of Classification Search
None
See application file for complete search history.

(56) References Cited

U.S. PATENT DOCUMENTS

| | | |
|---|---|---|
| 5,736,369 A | 4/1998 | Bowen et al. |
| 6,635,806 B1 | 10/2003 | Kriz et al. |
| 6,858,777 B2 | 2/2005 | Zhong et al. |
| 2003/0110531 A1 | 6/2003 | Dan et al. |
| 2008/0014633 A1 | 1/2008 | Spangenberg et al. |
| 2012/0124696 A1 | 5/2012 | Ishida et al. |
| 2012/0297506 A1 | 11/2012 | Dan et al. |
| 2014/0068797 A1 | 3/2014 | Doudna et al. |
| 2014/0176772 A1 | 6/2014 | Abe |
| 2015/0267214 A1 | 9/2015 | Bendich et al. |
| 2016/0208243 A1 | 7/2016 | Zhang et al. |
| 2016/0355832 A1 | 12/2016 | Dan et al. |
| 2017/0073670 A1 | 3/2017 | Nishida et al. |
| 2017/0260535 A1 | 9/2017 | Xu et al. |
| 2018/0142248 A1 | 5/2018 | Martin-Ortigosa et al. |
| 2018/0223295 A1 | 8/2018 | Harling et al. |
| 2019/0062765 A1 | 2/2019 | Hamada et al. |
| 2019/0062766 A1 | 2/2019 | Hamada et al. |

FOREIGN PATENT DOCUMENTS

| | | |
|---|---|---|
| DE | 102015006335 A1 | 11/2016 |
| DE | 102015014252 A1 | 5/2017 |
| JP | H10503374 A | 3/1998 |
| JP | 2002533057 A | 10/2002 |
| JP | 2004-506427 | 3/2004 |
| JP | 2008-212048 | 9/2008 |
| JP | 2010524474 A | 7/2010 |
| JP | 2015523856 A | 8/2015 |
| JP | 2017-205103 | 11/2017 |
| JP | 2017-205104 | 11/2017 |
| WO | 95006127 A1 | 3/1995 |
| WO | 9604392 A2 | 2/1996 |
| WO | 2002052025 A2 | 7/2002 |
| WO | 2003007698 A2 | 1/2003 |
| WO | 2005024034 A1 | 3/2005 |
| WO | 2011013764 A1 | 2/2011 |
| WO | 2013169802 A1 | 11/2013 |
| WO | 2014065857 A1 | 5/2014 |
| WO | 2014144987 A2 | 9/2014 |
| WO | 2015133554 A1 | 9/2015 |

(Continued)

OTHER PUBLICATIONS https://micronmetals.com/products/tungsten-metal-powder/ retrieved Sep. 13, 2020. (Year: 2020).*
Rajasekaran "Biolistic transformation of cotton zygotic embryo meristem." Transgenic Cotton. Humana Press, Totowa, NJ, 2013. 47-57. (Year: 2013).*
Rech, et al. (Nature protocols 3.3 (2008): 410). (Year: 2008).*
Chian, et al. (Plant Molecular Biology Reporter 13.1 (1995): 31-37). (Year: 1995).*
Twyman, et al. ("Plant transformation technology: particle bombardment." Handbook of Plant Biotechnology (2004)). (Year: 2004).*
Lowe, et al. (Bio/technology 13.7 (1995): 677-682). (Year: 1995).*
Chowrira, et al. (Molecular biotechnology 3.1 (1995): 17-23). (Year: 1995).*
Romano, et al. (Plant Cell Reports 20.3 (2001): 198-204). (Year: 2001).*

(Continued)

*Primary Examiner* — Charles Logsdon
(74) *Attorney, Agent, or Firm* — Hamre, Schumann, Mueller & Larson, P.C.

(57) ABSTRACT

A method to transforming a plant includes coating a microparticle having a diameter of 0.3 to 0.9 μm with at least one type of nucleic acid, bombarding a shoot apex of the plant with the coated microparticle using a gene gun, growing the shoot apex bombarded with the coated microparticle to obtain a plant body, and selecting a transformed plant body from the plant body. The shoot apex is selected from the group consisting of a shoot apex of an embryo of a fully mature seed, a shoot apex of a young bud of a tuber, and a shoot apex of a terminal bud or a lateral bud.

14 Claims, 6 Drawing Sheets

Specification includes a Sequence Listing.

(56) References Cited

FOREIGN PATENT DOCUMENTS

| WO | 2015171894 A1 | 11/2015 |
|---|---|---|
| WO | 2017090761 A1 | 6/2017 |

OTHER PUBLICATIONS

H.D. Jones et al., "Wheat transformation: current technology and applications to grain development and composition"; Journal of Cereal Science, vol. 41, No. 2, pp. 137-147; Mar. 1, 2005 (11 pages).
F. Mahdavi et al., "Optimization of particle bombardment parameters for DNA delivery into the male flowers of banana"; Biologia, vol. 69, No. 7, pp. 888-894; Jan. 1, 2014 (7 pages).
Extended European Search Report issued in corresponding European Application No. 17796263.6, dated Nov. 27, 2019 (9 pages).
E.L. Rech et al., "High-efficiency transformation by biolistics of soybean, common bean and cotton transgenic plants," Nature Protocols, 2008, vol. 3, No. 3, pp. 410-418 (9 pages).
D.R. Russell et al., "Stable transformation of Phaseolus vulgaris via electric-discharge mediated particle acceleration," Plant Cell Reports, 1993, vol. 12, pp. 165-169 (5 pages).
J.W. Kim et al., "Stable Delivery of a Canavalin Promoter-β-Glucuronidase Gene Fusion into French Bean by Particle Bombardment," Plant Cell Physiol., 1997, vol. 38, No. 1, pp. 70-75 (6 pages).
J.W. Kim et al., "Transformation and regeneration of French bean plants by the particle bombardment process," Plant Science, 1996, vol. 117, pp. 131-138 (8 pages).
K. Lowe et al., "Germline Transformation of Maize Following Manipulation of Chimeric Shoot Meristems," Biotechnology, 1995, vol. 13, pp. 677-682 (6 pages).
G.S. Brar et al., "Recovery of transgenic peanut (*Arachis hypogaea* L.) plants from elite cultivars utilizing ACCELL® technology," The Plant Journal, 1994, vol. 5, No. 5, pp. 745-753 (9 pages).
T. Hasegawa et al., "Production of Transgenic Carnation Introduced Sarcotoxin Gene through Particle Bombardment," Research Bulletin of the Aichi-ken Agricultural Research Center, 2003, vol. 35, pp. 143-147 (6 pages).
H. Zhong et al., "The pea (*Pisum sativum* L.) rbcS transit peptide directs the Alcaligenes eutrophus polyhydroxybutyrate enzymes into the maize (*Zea mays* L.) chloroplasts," Plant Science, 2003, vol. 165, pp. 455-462 (8 pages).
R. Bilang et al., "Transient gene expression in vegetative shoot apical meristems of wheat after ballistic microtargeting," The Plant Journal, 1993, vol. 4, No. 4, pp. 735-744 (10 pages).
International Search Report issued in International Application No. PCT/JP2017/018262; dated Aug. 8, 2017 (3 pages).
Written Opinion of the International Search Authority issued in International Application No. PCT/JP2017/018262; dated Aug. 8, 2017 (6 pages).
P. Supartana et al. "Development of Simple and Efficient in Planta Transformation Method for Rice (*Orzya sativa* L.) Using Agrobacterium tumefaciens"; Journal of Bioscience and Bioengineering, vol. 100, No. 4, pp. 391-397; Jun. 2005 (7 pages).
T. Komiya; "Development of Apple Tissue Culture Techniques and Their Applications," Plant Tissue Culture Letters, vol. 9, issue 2, pp. 69-73; Jun. 19, 1992 (6 pages) with partial translation.
International Preliminary Report on Patentability issued in International Application No. PCT/JP2017/018262; dated Nov. 22, 2018 (10 pages).
Written Opinion of the International Search Authority issued in International Application No. PCT/JP2017/018263, dated Aug. 15, 2017 (9 pages).
International Preliminary Report on Patentability issued in International Application No. PCT/JP2017/018263; dated Nov. 22, 2018 (16 pages).
C. Sautter et al., "Shoot apical meristems as a target for gene transfer by microballistics", Euphytica, Kluwer Academic Publishers, vol. 85, No. 1-3, pp. 45-51; Jan. 1, 1995 (7 pages).
Partial European Search Report issued in corresponding European Application No. 17796264.4; dated Nov. 6, 2019 (15 pages).
C.P. Petrillo et al.,"Optimization of particle bombardment parameters for the genetic transformation of Brazilian maize inbred lines," Pesquisa Agropecuaria Brasileira, vol. 43, No. 3, pp. 371-378, Mar. 1, 2008 (8 pages).
European Office Action issued in corresponding European Application No. 17796263.6; dated Jul. 1, 2020 (6 pages).
M.B. Sticklen et al., "Shoot Apical Meristem: A Sustainable Explant for Genetic Transformation of Cereal Crops", In Vitro Cellular & Development Biology—Plant; vol. 41, No. 3, pp. 187-200; May 1, 2005 (14 pages).
K. Rajasekaran, "Biolistic Transformation of Cotton Zygotic Embryo Meristem", Transgenic Cotton: Methods and Protocols, Methods in Molecular Biology, vol. 958, pp. 47-57; Oct. 16, 2012 (11 pages).
R. Imai, "Genome editing in wheat—Development of an in planta transformation technique for direct introduction of editing enzymes", Agricultural biotechnology, Jan. 20, 2017, vol. 1, pp. 17-18 (7 pages) with English Partial Translation.
International Search Report issued in International Application No. PCT/JP2017/018263, dated Aug. 15, 2017 (6 pages).
W. Yang et al., "Control of Rice Embryo Development, Shoot Apical Meristem Maintenance, and Grain Yield by a Novel Cytochrome P450," Molecular Plant, vol. 6, No. 6, pp. 1945-1960, Nov. 2013 (17 pages).
A. Romano et al., "Transformation of potato (*Solanum tuberosum*) using particle bombardment," Plant Cell Reports, vol. 20, pp. 198-204, Feb. 20, 2001 (7 pages).
P. Teper-Bamnolker et al., "Release of a Apical Dominance in Potato Tuber Is Accompanied by Programmed Cell Death in the Apical Bud Meristem [C] [W]," Plant Physiology, vol. 158, pp. 2053-2067, Apr. 2012 (15 pages).
H.J. Tillich et al., "Seedling Diversity and the Homologies of Seedling Organs in the Order Poales (Monocotyledons)," Annals of Botany, vol. 100, pp. 1413-1429, Oct. 12, 2007 (17 pages).
M. Lakshmanan et al., "Rapid and Efficient Gene Delivery into Plant Cells Using Designed Peptide Carriers," Biomacromolecules, vol. 14, pp. 10-16, 2013 (7 pages).
Office Action issued in corresponding Domestic U.S. Appl. No. 16/189,225; dated Jun. 10, 2020 (18 pages).
A. Romano et al., "Transformation of potato (*Solanum tuberosum*) using particle bombardment", Plant Cell Reports, 2001, vol. 20, pp. 198-204 (7 pages).
P. Teper-Bamnolker et al., "Release of Apical Dominance in Potato Tuber Is Accompanied by Programmed Cell Death in the Apical Bud Meristem", Plant Physiology, Apr. 2012, vol. 158, pp. 2053-2067 (15 pages).
M. Lakshmanan et al., "Rapid and Efficient Gene Delivery into Plant Cells Using Designed Peptide Carriers", ACS publications, Biomacromolecules, 2013, vol. 14, pp. 10-16 (7 pages).
W. Yang et al., "Control of Rice Embryo Development, Shoot Apical Meristem Maintenance, and Grain Yield by a Novel Cytochrome P450", Molecular Plant, vol. 6, No. 6, pp. 1945-1960 (17 pages).
H-J. Tillich, "Seedling Diversity and the Homologies of Seedling Organs in the Order Poales (Monocotyledons)", Annals of Botany, 2007, vol. 100, pp. 1413-1429 (17 pages).
Office Action issued in U.S. Appl. No. 16/189,225, dated Dec. 11, 2020 (21 pages).
Office Action issued in domestic U.S. Appl. No. 16/733,993; dated Sep. 23, 2020 (29 pages).
Notification of Reasons for Refusal issued in Japanese Patent Application No. 2017-096887, dated Apr. 27, 2021 (14 pages).
Office Action issued in corresponding EP Application No. 17796264.4, dated Feb. 18, 2021 (6 pages).
Bulletin of Hokkaido Research Organization Agricultural Experiment Stations, "Introduction of the plasmid DNA by Electroporation into Potato Mesophyll Protoplasts," vol. 62, pp. 69-77, 1991, with English summary (9 pages).
Sailaja, M., et al., "Stable genetic transformation of castor (*Ricinus communis* L.) via particle gun-mediated gene transfer using embryo axes from mature seeds," Plant Cell Rep, vol. 27, pp. 1509-1519, 2008 (11 pages).
Office Action issued in corresponding Japanese Patent Application No. 2017-096886, dated Mar. 2, 2021, with English translation (10 pages).

(56) References Cited

OTHER PUBLICATIONS

Office Action issued in corresponding U.S. Appl. No. 16/733,993, dated Apr. 2, 2021 (34 pages).
Office Action issued in corresponding U.S. Appl. No. 16/733,993, dated Jul. 21, 2021 (36 pages).
Caryl A. Chian et al., "A Procedure for Biolistic Transformation and Regeneration of Transgenic Cotton from Meristematic Tissue", Plant Molecular Biology Reporter 13.1 (1995): 31-37 (7 pages).
Applicant-Initiated Interview Summary issued in U.S. Appl. No. 16/189,225, dated Apr. 30, 2021, 4 pages.
Vianna et al., "Fragment DNA as vector for genetic transformation of bean (*Phaseolus vulgaris* L.)" from Scientia Horticulturae, dated Jun. 11, 2003, 8 pages, cited in Applicant-Initiated Interview Summary issued in U.S. Appl. No. 16/189,225.
Office Action issued in U.S. Appl. No. 16/189,225, dated Jul. 30, 2021, 20 pages.
Hamada, et al., "An in planta biolistic method for stable wheat transformation" Scientific Reports, 7:11443, Sep. 13, 2017, 8 pages.
International Search Report and Written Opinion issued in International Application No. PCT/JP2020/049058, dated Mar. 2, 2021, 20 pages w/translations.
Final Rejection issued in U.S. Appl. No. 16/189,225, dated Aug. 4, 2022, 26 pages.
Notice of Allowance issued in co-pending U.S. Appl. No. 16/733,993, dated Apr. 18, 2022, 21 pages.
Office Action issued in co-pending U.S. Appl. No. 16/189,225, dated Feb. 22, 2022, 28 pages.
Sharma, et al., "APOBEC3A cytidine deaminase induces RNA editing in monocytes and macrophages", Nature Communications, pp. 1-15.
Dhir, et al, "Optimization and transformation of Arundo donax L. using particle bombardment", African Journal of Biotechnology, vol. 9, No. 39, pp. 6460-6469, Sep. 27, 2010.
Takenaka, et al., "The process of RNA editing in plant mitochondria", Mitochondrion, vol. 8, 2008, pp. 35-46.

\* cited by examiner

W: Wild type strain
FG1-5:Transgene-detected Individuals

SEQUENCE LISTING

```
<160> NUMBER OF SEQ ID NOS: 7

<210> SEQ ID NO 1
<211> LENGTH: 19
<212> TYPE: DNA
<213> ORGANISM: Artificial Sequence
<220> FEATURE:
<223> OTHER INFORMATION: GFP forward primer

<400> SEQUENCE: 1
acggccacaa gttcagcgt                                              19

<210> SEQ ID NO 2
<211> LENGTH: 19
<212> TYPE: DNA
```

```
<213> ORGANISM: Artificial Sequence
<220> FEATURE:
<223> OTHER INFORMATION: GFP reverse primer

<400> SEQUENCE: 2
accatgtgat cgcgcttct                                                  19

<210> SEQ ID NO 3
<211> LENGTH: 5646
<212> TYPE: DNA
<213> ORGANISM: Artificial Sequence
<220> FEATURE:
<223> OTHER INFORMATION: chimeric GFP vector

<400> SEQUENCE: 3
tcttccgctt cctcgctcac tgactcgctg cgctcggtcg ttcggctgcg gcgagcggta      60
tcagctcact caaaggcggt aatacggtta tccacagaat caggggataa cgcaggaaag     120
aacatgtgag caaaaggcca gcaaaaggcc aggaaccgta aaaaggccgc gttgctggcg     180 ttttttccata ggctccgccc ccctgacgag catcacaaaa atcgacgctc aagtcagagg    240
tggcgaaacc cgacaggact ataaagatac caggcgtttc cccctggaag ctccctcgtg     300
cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaaccccc gttcagcccg accgctgcgc cttatccggt     480
aactatcgtc ttgagtccaa cccggtaaga cgacttat cgccactggc agcagccact      540
ggtaacagga ttagcagagc gaggtatgta ggcggtgcta cagagttctt gaagtggtgg    600
cctaactacg gctacactag aaggacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
```

```
tacatatttg aatgtattta gaaaaataaa caaatagggg ttccgcgcac atttccccga   1920
aaagtgccac ctgacgtcta agaaaccatt attatcatga cattaaccta taaaaatagg   1980
cgtatcacga ggccctttcg tctcgcgcgt ttcggtgatg acggtgaaaa cctctgacac   2040
atgcagctcc cggagacggt cacagcttgt ctgtaagcgg atgccgggag cagacaagcc   2100
cgtcagggcg cgtcagcggg tgttggcggg tgtcggggct ggcttaacta tgcggcatca   2160
gagcagattg tactgagagt gcaccatatg cggtgtgaaa taccgcacag atgcgtaagg   2220
agaaaatacc gcatcaggcg ccattcgcca ttcaggctgc gcaactgttg ggaagggcga   2280
tcggtgcggg cctcttcgct attacgccag ctggcgaaag ggggatgtgc tgcaaggcga   2340
ttaagttggg taacgccagg gttttcccag tcacgacgtt gtaaaacgac ggccagtgcc   2400
aagcttgcat gcctgcagtg cagcgtgacc cggtcgtgcc cctctctaga gataatgagc   2460
attgcatgtc taagttataa aaattaccha catatttttt ttgtcacact tgtttgaagt   2520
gcagtttatc tatctttata catatattta aactttactc tacgaataat ataatctata   2580
gtactacaat aatatcagtg ttttagagaa tcatataaat gaacagttag acatggtcta   2640
aaggacaatt gagtattttg acaacaggac tctacagttt tatctttta gtgtgcatgt   2700
gttctccttt tttttgcaa atagcttcac ctatataata cttcatccat tttattagta   2760
catccattta gggtttaggg ttaatggttt ttatagacta atttttttag tacatctatt   2820
ttattctatt ttagcctcta aattaagaaa actaaaactc tattttagtt tttttattta   2880
ataatttaga tataaaatag aataaaataa agtgactaaa aattaaacaa atacccttta   2940
agaaattaaa aaaactaagg aaacattttt cttgtttcga gtagataatg ccagcctgtt   3000
aaacgccgtc gacgagtcta acggacacca accagcgaac cagcagcgtc gcgtcgggcc   3060
aagcgaagca gacggcacgg catctctgtc gctgcctctg gaccctctc gagagttccg   3120
ctccaccgtt ggacttgctc cgctgtcggc atccagaaat tgcgtggcgg agcggcagac   3180
gtgagccggc acggcaggcg gcctcctcct cctctcacgg cacggcagct acgggggatt   3240
ccttcccac cgctccttcg ctttcccttc ctcgcccgcc gtaataaata gacaccccct   3300
ccacaccctc tttcccaac ctcgtgttgt tcggagcgca cacacacaca accagatctc   3360
ccccaaatcc acccgtcggc acctccgctt caaggtacgc cgctcgtcct ccccccccc   3420
ccctctctac cttctctaga tcggcgttcc ggtccatggt tagggcccgg tagttctact   3480
tctgttcatg tttgtgttag atccgtgttt gtgttagatc cgtgctgcta gcgttcgtac   3540
acggatgcga cctgtacgtc agacacgttc tgattgctaa cttgccagtg tttctctttg   3600
gggaatcctg ggatggctct agccgttccg cagacgggat cgatttcatg attttttttg   3660
tttcgttgca tagggtttgg tttgcccttt tcctttattt caatatatgc cgtgcacttg   3720
tttgtcgggt catcttttca tgctttttt tgtcttggtt gtgatgatgt ggtctggttg   3780
ggcggtcgtt ctagatcgga gtagaattct gtttcaaact acctggtgga tttattaatt   3840
ttggatctgt atgtgtgtgc catacatatt catagttacg aattgaagat gatggatgga   3900
aatatcgatc taggataggt atacatgttg atgcgggttt tactgatgca tatacagaga   3960
tgcttttgt tcgcttggtt gtgatgatgt ggtgtggttg ggcggtcgtt cattcgttct   4020
agatcggagt agaatactgt ttcaaactac ctggtgtatt tattaatttt ggaactgtat   4080
gtgtgtgtca tacatcttca tagttacgag tttaagatgg atggaaatat cgatctagga   4140
taggtataca tgttgatgtg ggttttactg atgcatatac atgatggcat atgcagcatc   4200
```

```
tattcatatg ctctaaccatt gagtacctat ctattataat aaacaagtat gttttataat    4260
tattttgatc ttgatatact tggatgatgg catatgcagc agctatatgt ggattttttt    4320
agccctgcct tcatacgcta tttatttgct tggtactgtt tcttttgtcg atgctcaccc    4380
tgttgtttgg tgttacttct gcaggtcgac tctagaggat ccatggtgag caagggcgag    4440
gagctgttca ccggggtggt gcccatcctg gtcgagctgg acggcgacgt aaacggccac    4500
aagttcagcg tgtccggcga gggcgagggc gatgccacct acggcaagct gaccctgaag    4560
ttcatctgca ccaccggcaa gctgcccgtg ccctggccca ccctcgtgac caccttcacc    4620
tacggcgtgc agtgcttcag ccgctacccc gaccacatga gcagcacga cttcttcaag    4680 tccgccatgc ccgaaggcta cgtccaggag cgcaccatct tcttcaagga cgacggcaac    4740
tacaagaccc gcgccgaggt gaagttcgag ggcgacaccc tggtgaaccg catcgagctg    4800
aagggcatcg acttcaagga ggacggcaac atcctggggc acaagctgga gtacaactac    4860
aacagccaca acgtctatat catggccgac aagcagaaga cggcatcaa ggtgaacttc    4920 aagatccgcc acaacatcga ggacggcagc gtgcagctcg ccgaccacta ccagcagaac    4980
acccccatcg gcgacggccc cgtgctgctg cccgacaacc actacctgag cacccagtcc    5040
gccctgagca agacccccaa cgagaagcgc gatcacatgg tcctgctgga gttcgtgacc    5100
gccgccggga tcactcacgg catggacgag ctgtacaagt aagagctcga atttccccga    5160
tcgttcaaac atttggcaat aaagtttctt aagattgaat cctgttgccg gtcttgcgat    5220
gattatcata tatttctg ttgattacgt taagcatgta ataattaaca tgtaatgcat    5280
gacgttattt atgagatggg ttttatgat tagagtcccg caattataca tttaatacgc    5340
gatagaaaac aaaatatagc gcgcaaacta ggataaatta tcgcgcgcgg tgtcatctat    5400
gttactagat cgaattcgta atcatggtca tagctgtttc ctgtgtgaaa ttgttatccg    5460
ctcacaattc cacacaacat acgagccgga agcataaagt gtaaagcctg gggtgcctaa    5520
tgagtgagct aactcacatt aattgcgttg cgctcactgc ccgctttcca gtcgggaaac    5580
ctgtcgtgcc agctgcatta atgaatcggc caacgcgcgg ggagaggcgg tttgcgtatt    5640
gggcgc                                                              5646
```

<210> SEQ ID NO 4
<211> LENGTH: 20
<212> TYPE: DNA
<213> ORGANISM: Artificial Sequence
<220> FEATURE:
<223> OTHER INFORMATION: ubiquitin promoter F

<400> SEQUENCE: 4
cgacggccag tgccaagctt                                                20

<210> SEQ ID NO 5
<211> LENGTH: 20
<212> TYPE: DNA
<213> ORGANISM: Artificial Sequence
<220> FEATURE:
<223> OTHER INFORMATION: nos terminator R

<400> SEQUENCE: 5
atgaccatga ttacgaattc                                                20

<210> SEQ ID NO 6
<211> LENGTH: 23
<212> TYPE: DNA
<213> ORGANISM: Artificial Sequence

```
<220> FEATURE:
<223> OTHER INFORMATION: vector specific primer 1

<400> SEQUENCE: 6
aagctagagt aagtagttcg cca                                             23

<210> SEQ ID NO 7
<211> LENGTH: 23
<212> TYPE: DNA
<213> ORGANISM: Artificial Sequence
<220> FEATURE:
<223> OTHER INFORMATION: vector specific primer 2

<400> SEQUENCE: 7
atactgtcct tctagtgtag ccg                                             23
```

METHOD FOR CREATING TRANSFORMED PLANT

TECHNICAL FIELD

One or more embodiments of the present invention relate to an in planta plant transformation method with a particle bombardment method.

BACKGROUND

It is currently widespread as a general method of plant transformation that methods in which an exogenous gene is introduced into an protoplast, callus, or tissue piece of in vitro culture, with an electroporation method, via *Agrobacterium tumefaciens* or with a particle bombardment method. However, even if a gene is introduced into a cell or a tissue by such methods, it is difficult to regenerate a plant body to produce a transformant due to the difficulty in tissue culture for some plant species. Also, the transformation efficiency is not sufficiently high and therefore a selective marker gene has to be introduced to perform a marker selection. Furthermore, a somatic mutation (somaclonal mutation) often occurs with the need of long-term tissue culture.

Therefore, from the viewpoint of a reduction in the effort to produce a transformed plant and the safety of a transformed plant, there has been a demand for the development of an in planta transformation method and a method for producing an in planta transformed plant body without the involvement of tissue culture.

On the other hand, it is also known for wheat, rice, and the like that transformation methods without calluses or tissue pieces of in vitro culture (in planta transformation methods). As such an in planta transformation method, a method in which a gene is directly introduced into an exposed shoot apex of immature embryo or fully mature embryo with a particle bombardment method is used is known (Non-Patent Document 1). Moreover, Patent Document 1 and Non-Patent Document 2 disclose a method for infecting a fully mature embryo immediately after germination with *Agrobacterium* to introduce a gene.

However, the methods disclosed in these documents largely depend on the skill of an operator in common, so that gene transfer efficiency is low and there is room for improvement of reproducibility. Moreover, in Non-Patent Document 1, it has not been demonstrated that the transgene is transmitted to a next generation. Due to these factors, the above-mentioned methods have not been widely used up to the present.

RELATED ART DOCUMENTS

Patent Documents

Patent Document 1: WO 2005/024034

Non-Patent Documents

Non-Patent Document 1: Bilang et al. (1993) Transient gene expression in vegetative shot apical meristems of wheat after ballistic microtargeting. Plant Journal (1993) 4, 735-744

Non-Patent Document 2: Supartana et al. (2005) Development of simple and efficient in planta transformation for rice (*Ozyza sativa* L.) using *Agrobacterium tumefaciencs*. Journal of Bioscience AND Bioengineering (2005) 4, 391-397

SUMMARY

One or more embodiments of the present invention provide a plant transformation method without calluses or tissue pieces in in vitro culture. One or more embodiments of the present invention also provide a plant transformation method without the introduction of a selective marker gene. One or more embodiments of the present invention further provide a method for producing a transformed plant with excellent reproducibility.

The inventors have conducted intensive investigation and achieved one or more embodiments of the present invention.

That is, one or more embodiments of the present invention provide the followings:

(1) A method for transforming a plant, comprising the steps of:
  coating a microparticle with a diameter of 0.3 μm or more and 0.9 μm or less with at least one type of nucleic acid;
  bombarding a shoot apex of an embryo of a fully mature seed or a shoot apex of a young bud of a tuber with the coated microparticle using a gene gun;
  growing the shoot apex bombarded with the coated microparticle to obtain a plant body; and
  selecting a transformed plant body from the plant body.

(2) The method of (1), characterized by a step of bombarding into a L2 cell in the shoot apex of the embryo of the fully mature seed or the shoot apex of the young bud of the tuber.

(3) The method of (1), characterized by a step of bombarding into a shoot apical stem cell that transits to a germ cell line in the shoot apex of the embryo of the fully mature seed or the shoot apex of the young bud of the tuber.

(4) The method as described in any of (1) to (3), wherein the shoot apex of the embryo of the fully mature seed is an exposed shoot apex in which an endosperm, a coleoptile, a leaf primordium, and an excess of scutellum are removed from the fully mature seed.

(5) The method as described in any one of (1) to (3), wherein the shoot apex of the young bud of the tuber is an exposed shoot apex in which a tuber and a leaf primordium is removed from the young bud of the tuber.

(6) The method as described in any one of (1) to (5), wherein the at least one type of nucleic acid is a linear DNA containing a nucleic acid cassette to be introduced.

(7) The method as described in any one of (1) to (6), wherein the linear DNA is a linear plasmid comprising nucleic acids of 0.8 kb or more and 1.2 kb or less added to both termini of a nucleic acid cassette to be introduced, respectively (8) The method as described in any one of (1) to (7), characterized in that the fully mature seed is a fully mature seed having a root in length of 1 mm or less.

(9) The method as described in any one of (1) to (8), characterized in that the plant is any one selected from the group consisting of wheat, barley rice, corn, soybean, potato, and apple.

(10) A method for producing a transformant of a plant using the method as described in any one of (1) to (9).

(11) A transformant produced by the production method of (10) (excluding those known at the time of filing).

According to the method of one or more embodiments of the present invention, a shoot apex of an embryo in a fully mature seed is used as a target of a particle bombardment method, thus making it possible to obtain a plant transformant with good reproducibility without the need for callus formation and a selective marker gene. According to one or more embodiments of the present invention, an intended gene can be efficiently introduced into shoot apical stem cells that transit to a germ cell lines in a shoot apex.

DETAILED DESCRIPTION OF EMBODIMENTS

Figure 1:
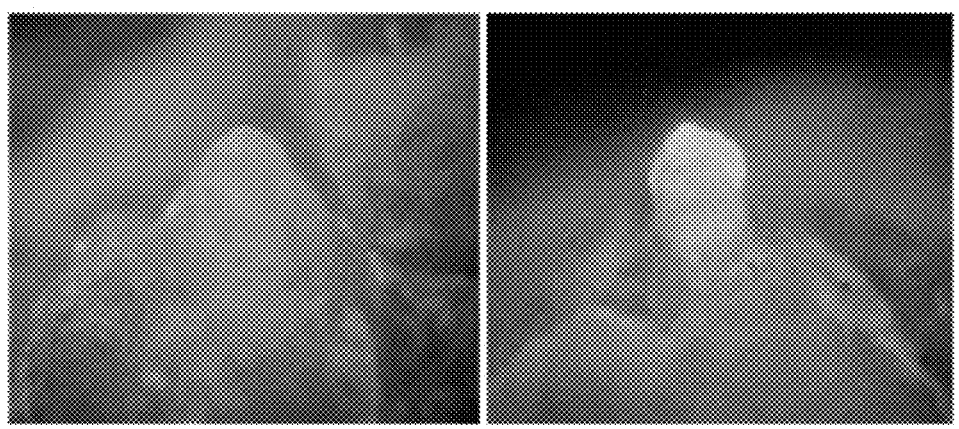
FIG. 1 is a diagram showing the appearance of GFP protein expression in a shoot apex in Example 1 according to one or more embodiments of the present invention.

Hereinafter, one or more embodiments of the present invention will be described in detail.

An in planta transformation method according to one or more embodiments of the present invention includes steps of allowing a fully mature seed of a plant to absorb water; and then exposing a shoot apex of an embryo in the seed; and then transforming cells of the shoot apex.

The "seed" as used herein encompasses not only a natural seed obtained by cultivating (or culturing) a plant under nature conditions or conditions close to natural conditions but also an artificial seed. In one or more embodiments, a natural seed is preferable. However, if an artificial seed from which a transformable shoot apex can be obtained is developed, such an artificial seed can be used. The natural seed includes not only a seed obtained in an outdoor field or the like, but also a seed obtained through greenhouse cultivation and a seed obtained from a tissue culture such as an in vitro seedling. A seed obtained through a direct reprogramming or the like can also be used as the seed of one or more embodiments of the present invention as long as a shoot apex can be obtained therefrom.

In one or more embodiments of the present invention, it is preferable to use a fully mature seed or a subterranean stem as a material to obtain a shoot apex. The "fully mature seed" refers to a seed that comes into full maturity in which the process of maturing alter pollination is completed. The "subterranean stem" collectively refers to stems in the underground, including a tuber, which is in a lump and has a plurality of buds; a corm, which is in a spherical shape and has a large terminal bud; and a bulb, which is in a spherical shape and has enlarged scaly leaves being attached to a shortened stem.

The "shoot apex" as used herein encompasses a growing point (shoot apical meristem) at the leading end of a stem, and a tissue including the growing point and several leaf primordia derived from the growing point. In one or more embodiments of the present invention, only a hemispherical (dome-shaped) growing point obtained by removing leaf primordia may be used as a shoot apex, or a shoot apex including a growing point and leaf primordia or a plant tissue including such a shoot apex may be used. A virus-free tissue is obtained by using only a growing point obtained by removing leaf primordia. Moreover, the "germ cell line" as used herein collectively refers to germ cells ranging from a primordial germ cell, which is the origin of a germ cell, to an oocyte and a spermatoblast, which are end products, and the "L2 layer" refers to the second cell layer from the outermost layer in a shoot apical meristem.

Step of Pre-Treatment for Transformation

The in planta transformation method according to one or more embodiments of the present invention can be applied to a wide variety of common seed-producing plants, plants that produces subterranean stems, and plants that can be subjected to shoot apex culture. Therefore, plants to be subjected to the in planta transformation method according to one or more embodiments of the present invention are spermatophytes including angiosperms and gymnosperms. Angiosperms include monocotyledons and dicotyledons. In general, an in planta transformation method is a method of transforming cells in a growing point in a plant growing state, without an operation for tissue culture. However, the "in planta transformation method" as used herein only encompasses those including a tissue culture method associated with shoot apex culture, but does not encompass those including any operation for other tissue cultures.

There is no limitation on the type of monocotyledon, and examples thereof include plants of Gramineae, Liliaceae, Musaceae, Bromeliaceae, and Orchidaceae.

Examples of the plants of Gramineae include rice, wheat, barley corn oat, Japanese lawn grass, sorghum, rye, millet, and sugar cane. Examples of the plants of Liliaceae include Welsh onion and asparagus. An example of the plants of Musaceae is banana. An example of the plants of Bromeliaceae is pineapple. Examples of the plants of Orchidaceae include orchids.

Examples of the dicotyledons include plants of Brassicaceae, Leguminosae, Solanaceae, Cucurbitaceae, Convolvulaceae, Rosaceae, Moraceae, Malvaceae, Asteraceae. Amaranthaceae, and Polygonaceae.

Examples of the plants of Brassicaceae include thale cress, Chinese cabbage, rape, cabbage, cauliflower, and Japanese radish. Examples of the plants of Legumineae include soybean, red mung bean, kidney bean, pea, black-eyed pea, and alfalfa. Examples of the plants of Solanaceae include tomato, eggplant, potato, tobacco, and red pepper. Examples of the plants of Cucurbitaceae include Oriental melon, cucumber, cantaloupe melon, and watermelon. Examples of the plants of Convolvulaceae include morning glory sweet potato (yam), and bindweed. Examples of the plants of Rosaceae include roses, strawberry and apple.

Examples of the plants of Moraceae include mulberry, fig, and rubber tree. Examples of the plants of Malvaceae include a cotton plant and kenaf. An example of the plants of Asteraceae is lettuce. An example of the plants of Amaranthaceae is beet (sugar beet). An example of the plants of Polygonaceae is buckwheat.

On the other hand, examples of the gymnosperms include pine, Japanese cedar, ginkgo, and cycad.

In the in planta transformation method according to one or more embodiments of the present invention, first, a fully mature seed of a plant is allowed to absorb water. A fully mature seed may be vernalized as necessary before allowed to absorb water. A seed is allowed to absorb water by soaking and incubating the seed with water. In one or more embodiments, the water absorption temperature is preferably 15 to 25° C. for wheat, barley, or rice, and preferably 25 to 35° C. for corn or soybean, for example. At this time, water may be replaced one or more times. Regarding the water absorption period, in the case of wheat, for example, it may be preferable to allow a seed to absorb water until before a radicle starts growing or until before a new leaf primordium is formed. When the water absorption period is expressed by amount of time for water absorption, a seed may be allowed to absorb water for less than 16 hours after the start of the water absorption, and preferably 12 hours, depending on the dormant state of the seed. This water absorption step allows the seed to be softened, thus making it easy to expose a shoot apex.

2. Step of Exposing Shoot Apex of Embryo in Seed

Then, a shoot apex of an embryo in the seed that has been allowed to absorb water as described above is exposed. For wheat, barley, rice, or corn, a shoot apex is exposed by removing coleoptiles and leaf primordia. For soybean, a shoot apex is exposed by removing a seed coat and cotyledons. For potato, a shoot apex is exposed by allowing a seed potato to sprout and removing leaf primordia from an isolated young bud. For apple, a shoot apex is exposed by removing leaf primordia from a seed embryo, or an isolated terminal bud or lateral bud. The means for exposing can be any means as long as a coleoptile and a leaf primordium, or a seed coat and a cotyledon can be removed therewith under a stereoscopic microscope, and examples of the means include punching tools such as a needle with a diameter of about 0.2 mm, tweezers, pipettes, syringes, and cutting tools such as a scalpel and a cutter. Then, an endosperm and an excess portion of a scutellum are removed by use of a cutting tool such as a scalpel, and the embryo, including the exposed shoot apex, and the scutellum are placed on an agar medium so that the shoot apex faces upward. In order to obtain a virus-free shoot apex, a scalpel may be replaced by a freshly sterilized scalpel at a final stage to isolate the shoot apex. In this case, a virus-free transformant can be obtained.

3. Step of Transforming Cells of Shoot Apex

There is no particular limitation on a technique for introducing an intended gene, and a known genetic engineering technique can be used. In general, a recombinant vector containing an intended gene is produced, and a nucleic acid (e.g., recombinant vector) or a protein can be introduced into a shoot apex of a fully mature embryo as a target using an *Agrobacterium* mediated method, an electroporation method, a particle bombardment method, a PEG-calcium phosphate method, a liposome method, a microinjection method, a whisker method, a plasma method, a laser injection method, or the like. For wheat, rice, corn, or soybean, a method for the introduction into an embryo of a fully mature seed with a particle bombardment method may be preferable from the viewpoint of transfer efficiency into a plant body. The particle bombardment method is also effective in introducing a gene into a potato shoot apex. The particle bombardment method is a method of bombarding a cellular tissue with metal microparticles coated with a gene, and is effective for a case where *Agrobacterium* infection efficiency is low, such as a case of monocotyledons.

There is no particular limitation on a vector used in one or more embodiments of the present invention, and examples thereof include pAL-based vectors (e.g., pAL51 and pAL156), pUC-based vectors (e.g., pUC18, pUC19, and pUC9), pBI-based vectors (e.g., pBI121, pBI121, pBI221, pBI2113, and pBI101.2), pPZP-based vectors pSMA-based vectors, intermediate vectors (e.g., pLGV23 Neo and pNCAT), cauliflower mosaic virus (CaMV), bean common mosaic virus (BGMV), and tobacco mosaic virus (TMV).

A vector containing an intended gene can be produced as described below, for example. In order to insert an intended gene into a vector, a method can be used in which a purified DNA is cleaved with an appropriate restriction enzyme, inserted into a restriction enzyme site or multicloning site of an appropriate vector DNA, and ligated to the vector. An intended gene may be inserted into an intermediate vector through double cross-over. TA cloning, In-Fusion coning, and the like may also be used.

There is no particular limitation on an intended gene as long as the expression of the gene or the inhibition of the expression of the gene is desired. The intended gene may be an endogenous gene or exogenous gene of a plant of interest. The exogenous gene may be derived from different species, and genes derived from animals, plants, microorganisms, viruses, and the like can be used, for example. Examples of such a gene include glycometabolism related genes, lipid metabolism related genes, useful substance (e.g., medicine, enzyme, pigment, and aroma component) producing genes, plant growth controlling (promoting/inhibiting) genes, flowering regulation related genes, disease-and-pest resistance (e.g., insect damage resistance, nematode disease resistance, mold (fungus) disease resistance, bacterial disease resistance, and virus (disease) resistance) genes, environmental stress (e.g., low temperature, high temperature, dryness, salt, photoinhibition, and ultraviolet rays) resistance genes, transporter genes, flour milling properties related genes, baking properties related genes, noodle-making properties related genes, and site-specific nuclease genes. The intended gene may also be introduced such that an antisense strand, ribozyme, RNAi, or the like instead of a sense strand is expressed depending on the purpose of the gene introduction.

The "genome editing" as used herein is a portion of the techniques called "new breeding techniques (NBT)", and includes, but not be limited to, disrupting a gene by cleaving a specific gene on a genome and introducing a mutation thereinto, or inserting or substituting a DNA fragment in a site-specific manner, using a meganuclease, CRISPR-CAS, or the like; or introducing a point mutation of interest with a high efficiency to modify a gene function by constructing an artificial enzyme complex via removing nuclease activity from the CRISPR system and adding thereto a deamination enzyme, deaminase, and expressing the complex in a cell, and the technique may be used as far as a genome can be edited therewith. Using the genome editing technique makes it possible to disrupt a gene of interest with a high efficiency. With the gene disruption, a gene of interest can be only disrupted without traces of gene recombination, and therefore, such gene-disrupted plants are not treated as recombinant plants in some countries. Moreover, with the genome editing, site-specific insertion or substitution of a DNA fragment can be efficiently performed by linking the respective fragments that are homologous to the respective sequences of the two sides of a cleaved sequence to the two sides of a DNA fragment to be introduced into that site, respectively.

In the sense described above, the genome editing can be regarded as a technique different from a conventional plant transformation method, such as a direct introduction method or an *Agrobacterium*-mediated method, in which an exogenous gene is incorporated in a substantially random manner, and it may be thought that the genome editing technique is excluded from the definition of a transformation method. The genome editing technique has a feature of including a step of cleaving a genome DNA using a nuclease capable of targeting a cleavage site, or a nuclease with a guide RNA, and can be distinguished from a conventional transformation method without a nuclease capable of targeting, or a nuclease with a guide RNA. The term "using a nuclease, or a nuclease with a guide RNA" as used herein means that a nuclease protein may be introduced into a cell, and a DNA and/or RNA encoding a nuclease gene may be introduced into a cell to express a nuclease protein. Also, regarding the guide RNA, it is construed that an RNA may be introduced into a cell, and a DNA capable of expressing a guide RNA may be introduced to express a guide RNA Examples of proteins encoded by the site-specific nuclease genes include a zinc finger nuclease, a protein having zinc finger nuclease activity, and a TAL effector nuclease (TALEN). The zinc finger nuclease is a fusion protein of several zinc finger motifs that recognize a specific base and a FokI nuclease. The TALLEN is a fusion protein of a Transcription Activator Like (TAL) effector and a FokI nuclease. A site-specific nuclease includes another additional targeting technology such as a meganuclease, RNA inducible CRISPR-Cas9, or a leucine zipper.

Editing a genome by introducing a site-specific nuclease into a cell using the transformation method according to one or more embodiments of the present invention, integrating it into a genome, and expressing it makes it possible to change or modify the expression of one or more gene products. Specifically for a cell that contains and expresses a DNA molecule encoding one or more gene products, a CRISPR-Cas system which may contain a Cas protein and one or more guide RNAs targeting the DNA molecule is introduced into the cell, so that the one or more guide RNAs target genome gene loci of the DNA molecule encoding the one or more gene products, and the Cas protein cleaves the genome gene loci of the DNA molecule encoding the one or more gene products, thus making it possible to change or modify the expression of the one or more gene products.

Cas protein and a guide RNA may be used in a naturally occurring manner (in combination), or may be used in combination that is not present in nature. In one or more embodiments of the present invention, the expression of two or more gene products may be changed or modified. The guide RNA may include a guide sequence fused to a tracr sequence.

In one or more embodiments, the guide RNA has a length of at least 15, 16, 17, 18, 19, or 20 nucleotides, and the maximum number of nucleotides is preferably 30 or less, more preferably 25 or less, even more preferably 22 or less, and the most preferably 20.

In one or more embodiments, a cell to be transformed is a plant cell, more preferably a cell in a shoot apical meristem, even more preferably a L2 cell in a shoot apical meristem, and the most preferably a cell that transits to a germ cell line in a shoot apical meristem.

In one or more embodiments of the present invention, the Cas protein may contain one or more nuclear localization signals (NLSs). In some embodiments, the Cas protein is a type-II CRISPR enzyme. In some embodiments, the Cas protein is a Cas9 protein. In some embodiments, the Cas9 protein is Cas9 of *Streptococcus pneumoniae* (*S. pneumoniae*), *Streptococcus pyagenes* (*S. pyogenes*), or *Streptococcus thermophilus* (*S. thermophilus*), and may also encompass mutant Cas9 derived from these organisms. The protein may be a Cas9 homolog or a Cas9 ortholog.

The Cas protein may be subjected to codon optimization for the expression in a eucaryotic cell. The Cas protein may direct the cleavage of one or two strands at a position where a target sequence is localized. In one or more embodiments of the present invention, the expression of a gene product is reduced, and the gene product is a protein.

In addition to an intended gene, a promoter, an enhancer, an insulator, an intron, a terminator, a poly A addition signal, a selective marker gene, and the like can be ligated to the vector.

A plurality of types of intended genes may be inserted into a single vector. A single microparticle may be coated with a plurality of types of recombinant vectors. For example, a recombinant vector containing an intended gene and a recombinant vector containing a drug resistance gene may be separately produced, and these recombinant vectors may be coated on microparticles in combination, and a plant tissue may be bombarded with such microparticles.

A promoter that is not derived from a plant may be used as long as a promoter is a DNA that can function in a plant body or a plant cell, and direct a constitutive expression or an expression in a specific tissue of a plant or at a specific growth stage of a plant. Specific examples thereof include a cauliflower mosaic virus (CaMV) 35S promoter, an E12-35S omega promoter, a promoter of nopaline synthase gene (Pnos), a ubiquitin promoter derived from corn, an actin promoter derived from rice, a PR protein promoter derived from tobacco, ADH, and a RuBisco promoter. A sequence that enhances translational activity, such as an omega sequence of a tobacco mosaic virus can be used to enhance the translation efficiency. Moreover, IRES (internal ribosomal entry site) can be inserted into a site on the 3' downstream side of a promoter and the 5' upstream side of a translation initiation codon as a translation initiation region to translate a protein from a plurality of coding regions.

The terminator is a sequence that can terminate the transcription of a gene transcribed by the above-mentioned promoter, and contains a poly A addition signal and examples of the terminator include the terminator of a nopaline synthase (NOS) gene, the terminator of an octopine synthase (OCS) gene, and a CaMV 35S terminator.

Examples of the selective marker gene include herbicide resistance genes (e.g., a bialaphos resisitance gene, a glyphosate resistance gene (EPSPS), and a sulfonylurea resistance gene (ALS)), drug resistance genes (e.g., a tetracycline resistance gene, an ampicillin resistance gene, a kanamycin resistance gene, a hygromycin resistance gene, a spectinomycin resistance gene, a chloramphenicol resistance gene, and a neomycin resistance gene), fluorescence or luminescence reporter genes (e.g., luciferase, β-galactosidase, β-glucuronidase (GUS), and green fluorescent protein (GFP)), and enzyme gene such as a neomycin phosphotransferase II (NPT II) and dihydrofolate reductase. However, with one or more embodiments of the present invention, a transformant can be produced without introducing a selective marker gene.

The vector containing an intended gene to be bombarded into a plant may be a cyclic plasmid, a linear DNA obtained by cleaving a plasmid with a restriction enzyme or the like, a nucleic acid cassette fragment obtained by excising only a DNA fragment to be introduced, or a DNA fragment obtained by adding a nucleic acid having a length of 0.8 kb or more and 1.2 kb or less to one or both ends of a cassette fragment. These DNA fragments may be those amplified by PCR In this case, there is no particular limitation on a nucleic acid to be added, and the nucleic acid may have a sequence derived from the vector, but a nucleic acid having a sequence of a target site to be introduced is favorably used. In one or more embodiments, the minimum length of a nucleic acid to be added to an end of a cassette fragment is 0.5 kb or more, preferably 0.8 kb or more, and more preferably 1.0 kb or more, and the maximum length thereof is 3.0 kb or less, preferably 2.0 kb or less, and even more preferably 1.5 kb or less.

The above-mentioned vector containing an intended gene is bombarded into a fully mature embryo of wheat using a particle bombardment method. The intended gene and/or protein can be coated on the surface of microparticles (microcarriers) and such microparticles (microcarriers) can be bombarded into plant cells using a gene gun. Metal microparticles are favorably used as the microparticles because they have high specific gravity to improve a cell penetration power, and they are chemically inert and thus less likely to harm a living organism. Gold particles, tungsten particles, and the like are particularly favorably used among the metal microparticles.

In the particle bombardment method, an intended gene can be introduced into a plant cell as follows. First, microparticles such as gold particles or tungsten particles are washed and sterilized, and a nucleic acid (e.g. recombinant vector, linear DNA, or RNA), $CaCl_2$), and spermidine are added to the microparticles while being stirred using a vortex mixer or the like so that the gold particles or tungsten particles are coated with the DNA, and then the particles are washed with ethanol.

In one or more embodiments, the particle diameter of the microparticles is preferably 0.3 µm or more and 0.9 µm or less, more preferably 0.4 µm or more, even more preferably 0.5 µm or more, and especially preferably 0.6 µm. The maximum particle diameter is more preferably 0.8 µm or less, even more preferably 0.7 µm or less, and especially preferably 0.6 µm.

The gold particles or tungsten particles are applied onto a macrocarrier film using Pipetman or the like as uniformly as possible and then dried in a sterile environment such as a clean bench. And, the macrocarrier film and a plate on which a targeted shoot apex of a fully mature embryo is placed are mounted in a particle bombardment apparatus, and then a high-pressure helium gas is shot from a gas accelerating tube toward the macrocarrier film. The macrocarrier film stops at a stopping plate, but the gold particles pass through the stopping plate and enter the target placed below the stopping plate, so that the intended gene is introduced thereinto.

Depending on the particle diameter of the microparticles, the distance between the stopping plate and the targeted shoot apex may be preferably 9 cm or less, more preferably 8 cm or less, even more preferably 7 cm or less, and especially preferably 6 cm or less, for example, and the minimum distance may be preferably 2 cm or more, more preferably 3 cm or more, and even more preferably 4 cm or more, for example. Regarding the distance between the stopping plate and the target, an optimum value can be determined as appropriate through transient expression experiment or the like depending on the type of microparticles, the particle diameter, gas pressure, and the like.

In one or more embodiments, the gas pressure is preferably 1,100 to 1,600 psi, and more preferably 1,200 to 1,500 psi, for example, depending on the type of microparticles and the distance to the target. Regarding the gas pressure, an optimum value can be determined as appropriate through transient expression experiment or the like depending on the type of microparticles, the type of target, the distance between the target and the stopping plate, and the like.

In the transformation method according to one or more embodiments of the present invention, the number of shot for bombarding a shoot apex with the microparticles may be preferably two shots or more, more preferably three shots or more, and even more preferably four shots or more. In one or more embodiments, the upper limit of shot for bombarding a shoot apex with the microparticles is preferably twenty shots or less, more preferably fifteen shots or less, and even more preferably ten shots or less. Regarding the number of shot for bombardments, an optimum number is determined as appropriate through transient expression experiment or the like.

In the cell bombarded with the microparticles, the nucleic acid is released from the microparticle and is integrated with a genome DNA, and is thus obtaining a transformed cell. However, when a nucleic acid such as geminivirus that is proliferated in a plasmid shape or an artificial chromosome is introduced, a cell may be transformed without the integration. Also, with the transformation method according to one or more embodiments of the present invention, an exogenous gene can be introduced into an organelle. In such a case, it may be preferable to use a gene to which a promoter that is expressed specifically in an organelle is linked in a functional manner.

The shoot apex of a fully mature embryo subjected to the transformation process is grown on an agar medium for about a month and then transferred to soil. A bombarded shoot apex can be grown on a normal medium without applying selective pressure using a drug or the like (i.e., on a medium free from antibiotics, plant hormones, or the like) to obtain a transformant, but a drug resistance gene may be further introduced. When a drug resistance gene is introduced, a drug can be used to selectively culture transformed cells. For example, a sulfonylurea-based herbicide, chlorsulfuron (the resistance against this herbicide can be acquired by introducing a mutated ALS gene (acetobutyrate synthase gene)), or the like is known as a selection drug suitable for shoot apex culture.

When a drug resistance gene is introduced, the drug resistance gene and the intended gene may be present in the same vector or separate vectors. When the drug resistance gene and the intended gene are inserted into separate vectors, and are integrated into separate chromosomes, there is an advantage that self-pollination or backcross is performed to produce progenies so that an intended gene-introduced plant individual and a drug resistance gene-carrying plant individual can be separately obtained.

With the above-described method, an intended gene-introduced plant body or a genome-edited plant body can be created. In the thus created plant, the intended gene is expressed stably or the expression of the intended gene is suppressed, which is normally inherited (transmitted) to progenies.

The gene transfer efficiency into wheat and the expression efficiency (transformation efficiency) of the intended gene can be evaluated as follows.

For the gene transfer efficiency a DNA is extracted from a grown individual that has been subjected to a transformation process, and the intended gene can be detected by PCR and/or electrophoresis or Southern blotting. The gene transfer efficiency is calculated from the number of explants used for the gene introduction and the number of grown individuals carrying an exogenous gene.

For the expression efficiency of the intended gene, the presence or absence of an RNA expressed from the intended gene is evaluated for the grown individual in which the gene introduction has been confirmed. The presence or absence of an RNA can be confirmed using an RT-PCR method, for example. It may be detected through Northern blotting.

Also, the presence or absence of a protein expressed from the intended gene can be evaluated. The presence or absence of a protein can be confirmed through staining of plant section, electrophoresis, ELISA, RIA, dot-immunobinding assay, and/or Western blotting. The expression efficiency (transformation efficiency) of the intended gene is calculated from the number of explants used for the gene introduction and the number of grown individuals in which the presence of a protein expressed from the intended gene has been confirmed.

EXAMPLES

Hereinafter, one or more embodiments of the present invention will be specifically described by way of examples, but the present invention is not limited to the examples.

Example 1: Investigation of Gold Particle Diameter Optimum for Gene Introduction In order to determine a suitable gold particle diameter, the presence or absence of GFP fluorescence in a shoot apex that had been subjected to a gene introduction process or the presence or absence of a transgene in a current generation ($T_0$ generation) was examined.

1. Study Using Transient Expression System of GFP Fluorescent Protein as Index (1) Preparation of Fully Mature Seed of Wheat Fully mature seeds of wheat (*Triticum aestivum* cv. Fielder) were immersed in Haiter (a hypochlorous acid concentration of 6%; manufactured by Kao Corporation), shaken at room temperature for 20 minutes and washed with sterile water in a clean bench. After having been washed, the seeds were placed on Kimtowel or filter paper moistened with sterile water, and incubated at 4° C. for 2 days for the breaking dormancy. Thereafter, the seeds were incubated at 22° C. for about 12 hours and then used in the following experiments.

(2) Exposure of Shoot Apex in Embryo of Fully Mature Seed

A coleoptile and the first to third leaf primordia in the embryonic moiety of each of the above-mentioned germinated seeds were removed using a leading end of a needle (with a diameter of 0.20 mm) under a stereoscopic microscope. Thereafter, an endosperm and an excess portion of a scutellum were removed using a sterile knife (or a sterile scalpel), and the shoot apex moiety was thus fully exposed. The thus obtained samples were placed on an MS-maltose medium (4.3 g/L MS salt, MS vitamin, 30 g/L maltose, 0.98 g/L MES, 3%/PPM (plant preservative mixture; Nacalai Tesque Inc.), 7.0 g/L phytagel (registered trademark; Sigma-Aldrich), pH 5.8) at 30 samples per plate.

(3) Gene Introduction

The gene introduction into the shoot apex of the fully mature embryo of wheat was performed using a particle bombardment method as described below.

In this example, a transgene used was a plasmid DNA (pUC-based plasmid) containing a fluorescence reporter gene GFP (S65T), which was designed to be expressed under the control of a corn ubiquitin promoter and the first intron. The terminator of a nopaline synthase (NOS) gene was added as a terminator.

First, 30 mg of each of 0.3- to 1.6-μm gold particles was weighed out, and 500 μL of 70% ethanol was added thereto and suspended well using a Vortex mixer. Then, the gold particles were precipitated through centrifugation, and the ethanol was removed. Thereafter, 500 μL of 50% glycerol was added, and a sterile gold particle solution was thus obtained.

A plasmid DNA solution (1 μg/μL) purified using Qiagen Plasmid Midi Kit (Qiagen) was placed into a 1.5-mL tube at 5 μg per 750 μg of the gold particles. The sterile gold particle-containing solution was thoroughly suspended using an ultrasonic generator (ultrasonic washer UW-25 manufactured by Taga Electric Co., Ltd.) before use, and placed into the above-mentioned tube in an appropriate amount and stirred with pipetting. Next, 25 μL of 2.5 M $CaCl_2$ (Nacalai Tesque) and 10 μL of 0.1 M Spermidine (Nacalai Tesque) per 750 μg of the gold particles were added to the above-mentioned tube. Immediately after mixing, the resultant mixture was vigorously suspended for 5 minutes using a Vortex mixer. The mixture was left to stand at room temperature for 10 minutes, and was then centrifuged at 9,100×g for 2 seconds. The supernatant was removed, and the precipitation was washed with 70% ethanol and then 99.5% ethanol. Lastly, the supernatant was removed, and 24 μL of 99.5% ethanol was added thereto and suspended well. In a clean bench, 6 μL of the suspension was poured to the center of a macrocarrier, and the macrocarrier was then air-dried.

The particle bombardment was performed with Biolistic (registered trademark) PDS-1000/He Particle Delivery System (BIO-RAD). Bombardment pressure was set to about 94.9 kgf/cm$^2$ (1,350 psi), and the distance to a target tissue was set to 5 cm (for particles with a diameter of 0.6 μm or more) or 3.5 cm (for particles with a diameter of less than 0.6 μm). The samples were bombarded with the particles at 4 shots per dish. After bombardment, the samples were left to stand overnight in a dark place at 22° C.

(4) Study of Transient Expression Efficiency of GFP Protein

The transfer efficiency of the GFP gene in the shoot apex was calculated through observing GFP fluorescence (excitation: 470/40, absorption: 525/50) in the shoot apex under a stereoscopic fluorescence microscope (MIZFL III manufactured by Leica) (FIG. 1). Out of the fully mature embryos subjected to the transformation process, that having 5 or more spots of GFP fluorescence observed in the shoot apex tissue was taken as a transgenic individual, and the gene transfer efficiency was calculated (number of transgenic individuals/number of processed fully mature embryos× 100). As a result, the gene transfer efficiencies in the shoot apex in the cases of the gold particles with diameters of 0.8 μm, 0.6 μm, and 0.3 μm were higher than those in the cases the gold particles with diameters of 1.6 μm and 1.0 μm (Table 1). In particular, when the gold particles with a diameter of 0.6 μm were used, the gene transfer efficiency in the shoot apex was 72.7%, which was the highest compared with those in the cases of the gold particles with different diameters (Table 1). Also, as described later, the gene transfer efficiency in the case of the gold particles with a diameter of 0.6 μm was higher than that in the case of the gold particles with a diameter of 1.0 μm.

TABLE 1

|  |  | Gold particles per shot (μg) | | |
|---|---|---|---|---|
|  |  | 187.5 | 375 | 562.5 |
| Gold particle diameter (μm) | 1.6 | 0.0% | 0.0% | 0.0% |
|  | 1.0 | 6.7% | 6.7% | 10.0% |
|  | 0.8 | 50.0% | 30.0% | 33.3% |
|  | 0.6 | 73.3% | 33.3% | 40.0% |
|  | 0.3 | 20.0% | 43.4% | 36.7% |

2. Study of $T_0$ Generation Plant Using Genomic PCR as Index (1) Preparation of Fully Mature Seed of Wheat This was performed in accordance with the method described in Example 1-1-(1).

(2) Exposure of Shoot Apex in Embryo of Fully Mature Seed

This was performed in accordance with the method described in Example 1-1-(2).

(3) Gene Introduction

This was performed in accordance with the method described in Example 1-1-(3), proviso that two types of gold particles, namely those with diameters of 0.6 μm and 1.0 μm, were used.

(4) Growth of Individual Subjected to Transformation Process

An individual that had been subjected to the transformation process was left to stand overnight, and was transferred to a disposable container for plant cell culture (Sigma) in which an MS-maltose medium was placed, and was grown in a ong-day condition (22° C., day length of 16 hours). After grown for 3 to 4 weeks, the individual was transferred to a pot in which seedling compost for gardening was placed at a time point when the second and third leaves were observed. Thereafter, the individual was grown in a long-day condition in a climatic chamber (24° C., day length of 16 hours, humidity of 50 to 70%) until the fourth to the sixth leaves were out.

(5) Presence or Absence of Transgene in Leaf of to Plant

In the obtained plant body the presence or absence of the GFP gene, which is a fluorescence reporter gene, was examined using a PCR method. A genomic DNA was extracted from the fourth to sixth leaves (50 mg) using a benzyl chloride method, and PCR reaction was performed using the genomic DNA as a template with primers produced based on the sequences specific to the GFP gene.

```
The sequence of the primer:
                             (SEQ ID NO: 1)
ACGGCCACAAGTTCAGCGT The sequence of the primer:
                             (SEQ ID NO: 2)
ACCATGTGATCGCGCTTCT
```

A PCR reaction mixture was prepared by mixing 20 ng of the genomic DNA, 0.25 U of ExTaqHS (registered trademark, TaKaRa), 1.5 μL of accompanying 10×buffer, 2 mM dNTPs, and the pair of primers (each 2.5 pmol) with sterile distilled water such that the total volume was 15 μl. In the PCR reaction, the PCR reaction mixture was treated at 95° C. for 3 minutes, and subjected to 33 cycles of reaction of 95° C. for 30 seconds, 60° C. for 30 seconds, and 72° C. for 1 minute using TaKaRa PCR Thermal Cycler Dice (registered trademark). After the PCR reaction, electrophoresis was performed on 1.0% agarose gel, and the PCR product was detected through ethidium bromide staining. The individual in which an expected 601-bp GFP gene fragment was detected was determined as a transgenic individual.

Regarding the two types of gold particles used for the gene introduction, namely those with diameters of 1.0 μm and 0.6 μm, the number of the transgenic individuals was determined, and used to calculate the gene transfer efficiency with respect to the number of the fully mature embryos subjected to the gene introduction process (number of transgenic individuals/number of processed fully mature embryos×100).

As a result, when the gold particles with a diameter of 1.0 μm were used, the transgene was not detected (Table 2). On the other hand, when the gold particles with a diameter of 0.6 μm were used, three individuals were detected as the transgene-detected individuals ($T_0$ generation) (the gene transfer efficiency of 1.4%) (Table 2). Therefore, it was found that the gene transfer efficiency was enhanced by use of the gold particles with a diameter of 0.6 μm, which had high transient expression efficiency in Example 1-1-(4), compared with the gold particles with a diameter of 1.0 μm.

TABLE 2

| Gold particle diameter (μm) | Individuals subjected to transformation | Transgene-detected Individuals ($T_0$ generation) | Gene transfer efficiency ($T_0$ generation) |
|---|---|---|---|
| 1.0 | 499 | 0 | 0 |
| 0.6 | 222 | 3 | 1.4% |

Example 2: Investigation of Gas Pressure Optimum for Gene Introduction

In order to determine a suitable gas pressure, the presence or absence of GFP fluorescence in a shoot apex that had been subjected to a gene introduction process and the presence or absence of a transgene in a current generation ($T_0$ generation) were examined.

1. Study Using Transient Expression System of GFP Fluorescent Protein as Index (1) Preparation of Fully Mature Seed of Wheat This was performed in accordance with the method described in Example 1-1-(1).

(2) Exposure of Shoot Apex in Embryo of Fully Mature Seed

This was performed in accordance with the method described in Example 1-1-(2).

(3) Gene Introduction

This was performed in accordance with the method described in Example 1-1-(3), proviso that the gold particles with a diameter of 0.6 μm were used, and the gas pressure was set to 1,100 psi or 1,350 psi.

(4) Study of Transient Expression Efficiency of GFP Protein

This was performed in accordance with the method described in Example 1-1-(4). As a result, the gene transfer efficiency as described in Example 1-1-(4) was 74.2% at a gas pressure of 1,350 psi, which was higher than 13.3% at a gas pressure of 1,100 psi (Table 3). Also, as described later, the gene transfer efficiency in the $T_0$ generation was higher at a gas pressure of 1,350 psi than at a gas pressure of 1,100 psi.

TABLE 3

| Gold particle diameter (μm) | Gas pressure (psi) | No. of Individuals subjected to transformation | No. (%) of individuals expressing GFP in shoot apex | No. (%) of $T_0$ generation transgenic individuals |
|---|---|---|---|---|
| 0.6 | 1,100 | 120 | 16 (13.3) | 1 (0.8) |
|  | 1,350 | 120 | 89 (74.2) | 5 (4.2) |

(1) Growth of Individual Subjected to Transformation Process

This was performed in accordance with the method described in Example 1-2-(4).

(2) Presence or Absence of Transgene in Leaf of to Plant

This was performed in accordance with the method described in Example 1-2-(5). As a result, the gene transfer efficiency as described in Example 1-2-(5) was 4.2% at a gas pressure of 1,350 psi, which was higher than 0.8% at a gas pressure of 1,100 psi (Table 3). Therefore, it was found that the gene transfer efficiency was enhanced by use of a gas pressure of 1,350 psi with which a high efficiency of transient expression of a GFP protein was obtained in Example 2-1-(4), compared with a gas pressure of 1,100 psi.

(3) Gene Introduction

This was performed in accordance with the method described in Example 1-1-(3), proviso that the gold particles with a diameter of 0.6 μm were used.

2. Study of $T_0$ and $T_1$ Generation Plants Using Genomic PCR as Index (1) Growth of Individual Subjected to Transformation Process The individual in which transient GFP fluorescence was observed in the shoot apex in Example 3-1-3) was grown in accordance with the method described in Example 1-(2)-4.

(2) Presence or Absence of Transgene in Leaf of $T_0$ Plant

This was performed in accordance with the method described in Example 1-2-(5). For the fully mature embryos subjected to the transformation process after the respective water absorption periods, the number of the transgene-detected individuals ($T_0$ generation) was determined and used to calculate the gene transfer efficiency with respect to the number of the fully mature embryos subjected to the gene introduction process (number of transgenic individuals/number of processed fully mature embryos×100). As a result, when the fully mature seeds after the 6- to 12-hour water absorption period and after the 12- to 18-hour water absorption period were used in the experiment, the gene transfer efficiencies were 3.1% and 1.3%, respectively (Table 4), and the gene transfer efficiency was particularly high with the fully mature embryo after the 6- to 12-hour water absorption period (Table 4).

TABLE 4

| Water absorption period (hr) | Seed root length (mm) | No. of processed individuals | Transgene-detected Individuals ($T_0$ generation) | Gene transfer efficiency ($T_0$ generation) | Transgene-detected Individuals ($T_1$ generation) | Gene transfer efficiency ($T_1$ generation) |
|---|---|---|---|---|---|---|
| 6-12 | ≤1.0 | 64 | 2 | 3.1% | 2 | 3.1% |
| 12-18 |  | 452 | 6 | 1.3% | 3 | 0.7% |

Example 3: Investigation of Water Absorption Period Optimum for Gene Introduction In order to determine a suitable water absorption period, the presence or absence of GFP fluorescence in a shoot apex that had been subjected to a gene introduction process and the presence or absence of a transgene in a current generation ($T_0$, generation) and a next generation ($T_1$ generation) were examined.

1. Preparation of Fully Mature Embryo and Operation of Gene Introduction (1) Preparation of Fully Mature Seed of Wheat Fully mature seeds of wheat (*Triticum aestivum* cv. Fielder) were immersed in Haiter (with a hypochlorous acid concentration of 6%), shaken at room temperature for 20 minutes, and washed with sterile water in a clean bench. After having been washed, the seeds were placed on Kimtowel or filter paper moistened with sterile water, and incubated at 4° C. for 2 days. Thereafter, the seeds were incubated at 22° C. for 6 to 12 hours or 12 to 18 hours, and then used in the following experiments. The length of a seminal root was evaluated by measuring the length of a radicle after cutting open a coleorhiza.

(2) Exposure of Shoot Apex in Embryo of Fully Mature Seed

This was performed in accordance with the method described in Example 1-1-(2).

(3) Presence or Absence of Transgene in Leaf of $T_1$ Plant

Figure 2:
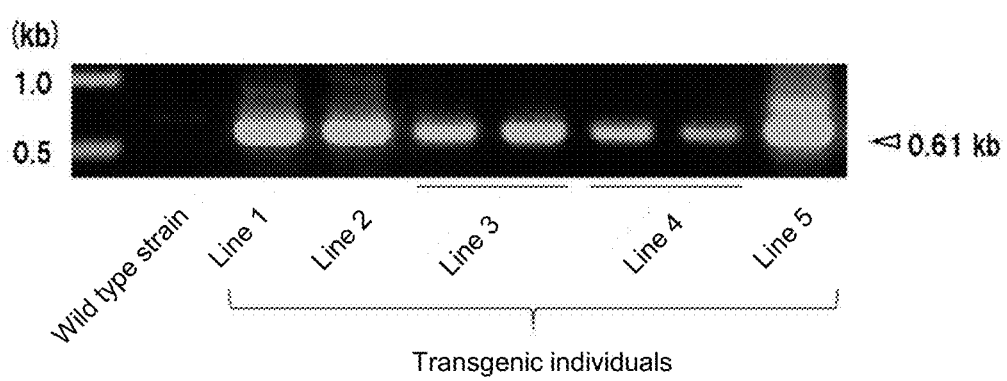
FIG. 2 is a diagram showing the results of the confirmation of the transgene in $T_1$ generation transformants in Example 2 according to one or more embodiments of the present invention, by a genomic PCR.

The transgene-detected individual in (2) above was grown, and $T_1$ seeds were obtained. About ten to twenty $T_1$ seeds were sowed and grown, and the first leaf (50 mg) was sampled. Genomic PCR and electrophoresis were performed in accordance with Example 1-(2)-5. The fully mature embryos after the respective water absorption periods were subjected to the transformation process, and the number of the transgene-detected individuals ($T_1$ generation) was determined and used to calculate the gene transfer efficiency with respect to the number of the fully mature embryos subjected to the gene introduction process (number of transgenic individuals/number of processed fully mature embryos×100). As a result, when the fully mature seeds after the 6- to 12-hour water absorption period and after the 12- to 18-hour water absorption period were used in the experiments, the gene transfer efficiencies were 3.1% (lines 1 and 2 in FIG. 2, Table 4) and 0.7% (lines 3 to 5 in FIG. 2, Table 4), respectively, and the gene transfer efficiency was particularly high with the fully mature embryo after the 6- to 12-hour water absorption period. It was determined from these results that the fully mature seed at the early stage of a water absorption period (between about 6 hours later and 18 hours later; a seminal root having a length of 1.0 mm or less) is suitable for the gene introduction, and the fully mature seed after 6- to 12-hour water adsorption period may be preferable.

Figure 3:
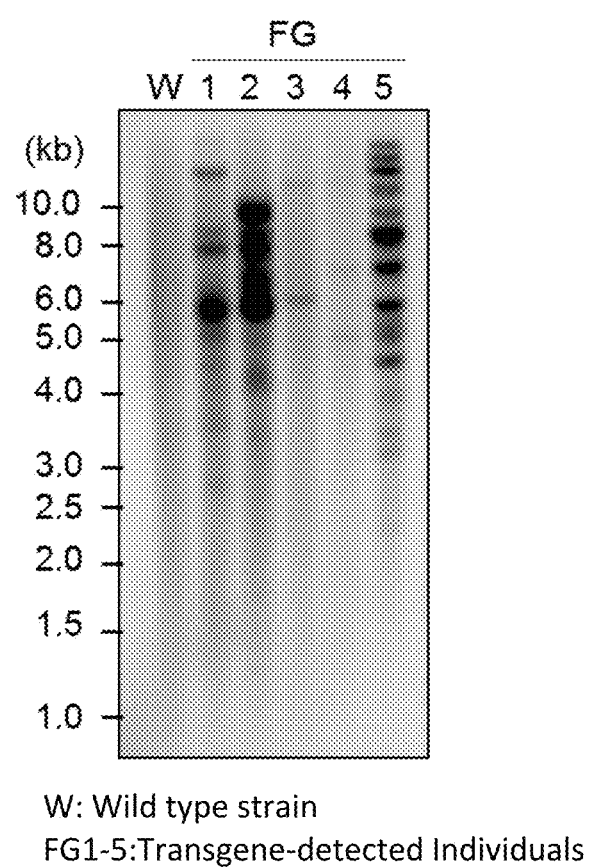
FIG. 3 is a photograph showing the result of Southern analysis for transgenic individuals (Example 3).

Regarding the five lines of the transgene-detected individuals ($T_1$ generation) shown in Table 4, the insertion of the GFP gene into the genomic DNA was confirmed through Southern blotting analysis with a probe of the GFP gene region (FIG. 3).

Example 4: Confirmation of Gene Expression in $T_1$ Generation

In the transformed wheat produced using the gene introduction method, the presence or absence of the expression of the transgene (GFP gene) was examined.

1. Observation of GFP Fluorescence in $T_1$ Seed

Figure 4A:
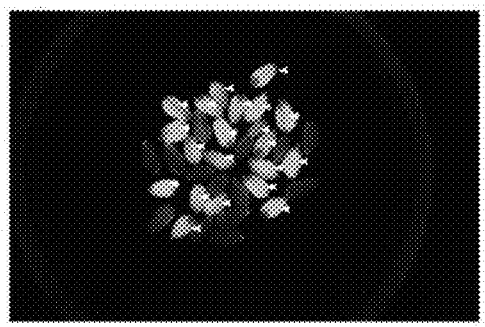
FIG. 4A is a photograph showing the whole of $T_1$ generation seeds in Example 4 according to one or more embodiments of the present invention, observed with GFP fluorescence.
Figure 4B:
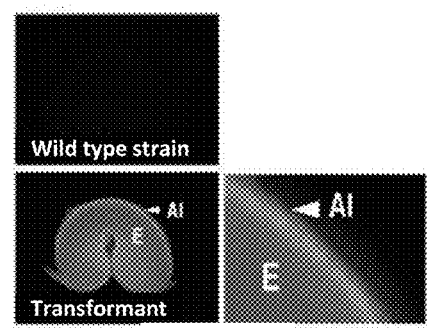
FIG. 4B is a photograph showing a half-cut of $T_1$ generation seed in Example 4 according to one or more embodiments of the present invention, observed with GFP fluorescence.

The $T_1$ seeds obtained in Example 3-2-(3) were placed on a sterile dish, and were observed for GFP fluorescence in the $T_1$ seeds under LAS 3000 (FujiFilm) (filter: 510DF10). As a result, GFP fluorescence was observed in the seeds (FIG. 4A). Next, the seed in which GFP fluorescence was observed was cut in half and was observed for GFP fluorescence (excitation: 470/40, absorption: 525/50) of the endosperm under a stereoscopic fluorescence microscope (MZFL III manufactured by Leica). As a result, GFP fluorescence was observed in the endosperm (E), and GFP fluorescence was intensively observed in the aleurone layer (Al) (FIG. 4B).

Figure 4C:
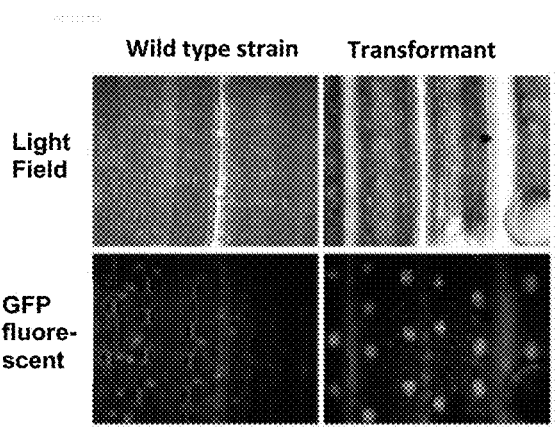
FIG. 4C is a photograph showing a $T_1$ generation young leaf in Example 4 according to one or more embodiments of the present invention, observed with GFP fluorescence.

2. Analysis of GFP Fluorescent Protein Expression in $T_1$ Generation Young Leaf Young leaves of the $T_1$ generation plant grown in Example 3-2-(3) were sampled, and were observed for GFP fluorescence (excitation: 470/40, absorption: 525/50) in the leaves under a stereoscopic fluorescence microscope (MZFL III manufactured by Leica). As a result, as shown in FIG. 4C, GFP fluorescence was observed in stomatal cells of the leaves in the genomic PCR-positive individual (transformant).

Next, total proteins were extracted from adult leaves of a wild-type strain and a transformant (transgenic individual) to detect a GFP fluorescent protein through Western blotting. First, 1 g of the adult leaf was frozen using liquid nitrogen and pulverized, and then was suspended in a protein extraction buffer (0.25 M sorbitol, 50 mM Tris/acetate, pH 7.5, 1 mM EDTA, 2 mM DTT, 1% PVP 10 µM PMSF). The extract was centrifuged (1,100×g, 15 minutes, 4° C.), and the supernatant was further centrifuged (12,800×g, 15 minutes, 4° C.). The supernatant obtained after this centrifugation was taken as a total protein fraction. Then, 20 µg of the total protein fraction was subjected to electrophoresis with 12.5% SDS-polyacrylamide gel, and transferred to a nitrocellulose membrane using a semidry method. The membrane was shaken in a blocking buffer (5% (w/v) Skim Milk Powder in TTBS (10 mM Tris-HCl 150 mM NaCl, 0.05% Tween-20, pH 7.5)) for 1 hour. After washing of the membrane with TTBS for 5 minutes was performed three times, a primary antibody was reacted with the membrane for 1 hour. After washing of the membrane with TTBS for 5 minutes was performed three times, a secondary antibody was reacted with the membrane for 1 hour. After washing of the membrane with TTBS for 5 minutes was performed three times, detection was performed in accordance with the instruction manual of Amersham ECL Western blotting analysis system (GE Healthcare). Mouse $IgG_1$ κ-derived GFP antibody (ROCHE) was used (2000-fold dilution) as the primary antibody, and peroxidase-labeled anti-mouse IgG antibody included in the above-mentioned kit was used (5000-fold dilution) as the secondary antibody.

Figure 4D:
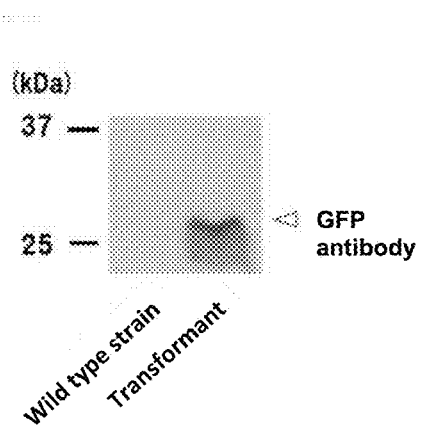
FIG. 4D is a photograph showing Western blotting for detecting GFP protein in a $T_1$ generation adult leaf in Example 4 according to one or more embodiments of the present invention.

As a result of Western blotting analysis, a signal was observed at near 27 kDa of an estimated molecular weight of the GFP protein, in the transformant, but no signals were detected in the wild-type strain (FIG. 4D). It was confirmed from these results that the transgene was normally expressed in the transformed plant produced using the above-described gene introduction method.

Transformants of barley, corn, rice, soybean, potato, and apple can also be obtained using substantially the same method as the method used to obtain a transformant of wheat.

Example 5: Confirmation of Genotypes of $T_1$ Generation Individuals Obtained from Single Line of $T_0$ Generation The transgenic individual ($T_0$ generation) produced using the method is a chimera, which is an individual in which cells having different genetic information coexist. Therefore, Southern blotting analysis was performed in order to examine whether or not a plurality of $T_1$ seeds obtained from a certain transgenic individual (To generation) had different genetic information.

$T_1$ seeds were harvested from spikes derived from the main stem and five tillers of an individual of line FG1 at $T_0$ generation obtained in Example 3-2-(3), and a plurality of individuals out of them were sowed. The sowed $T_1$ generation individuals were grown, and the presence or absence of the transgene in the $T_1$ generation individuals was examined in accordance with the method described in Example 3-2-(3). As a result, the transgene was detected in the $T_1$ individuals harvested from the spikes derived from the main stem and tillers other than tiller 2 (Table 5).

TABLE 5

| Source of spikes | No. of $T_1$ seeds harvested from spike | No. of $T_1$ seeds analyzed | Transgenic individuals ($T_0$ generation) |
|---|---|---|---|
| Main stem | 35 | 31 | 26 |
| Tiller 1 | 25 | 24 | 6 |
| Tiller 2 | 25 | 25 | 0 |
| Tiller 3 | 27 | 27 | 22 |
| Tiller 4 | 23 | 23 | 22 |
| Tiller 5 | 7 | 7 | 5 |

Figure 5A:
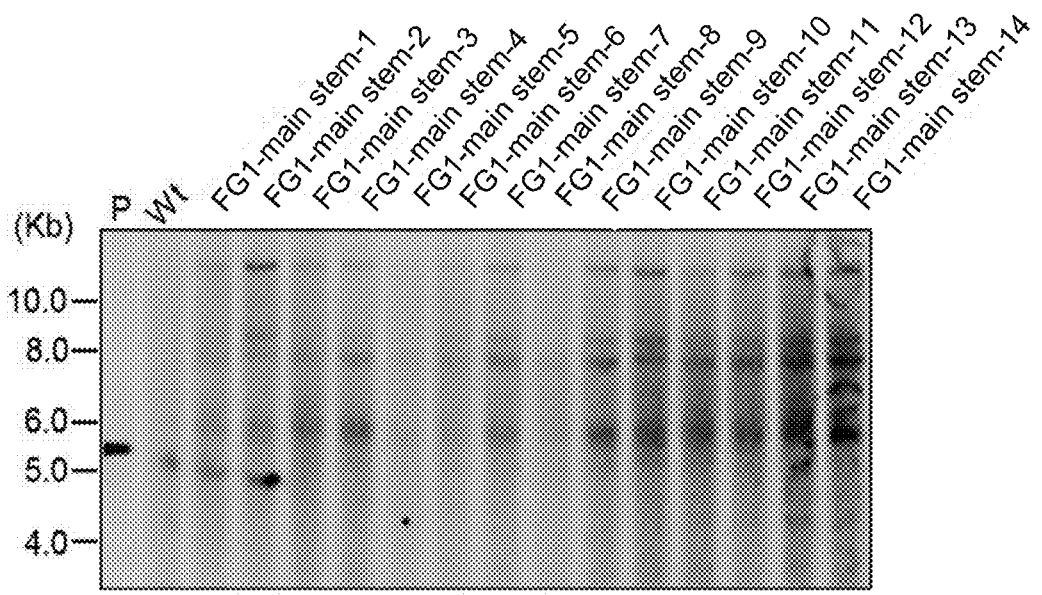
FIG. 5A is a photograph showing the results of Southern analysis of genomic DNAs obtained from young leaves of $T_1$ seeds derived from a main stem.
Figure 5B:
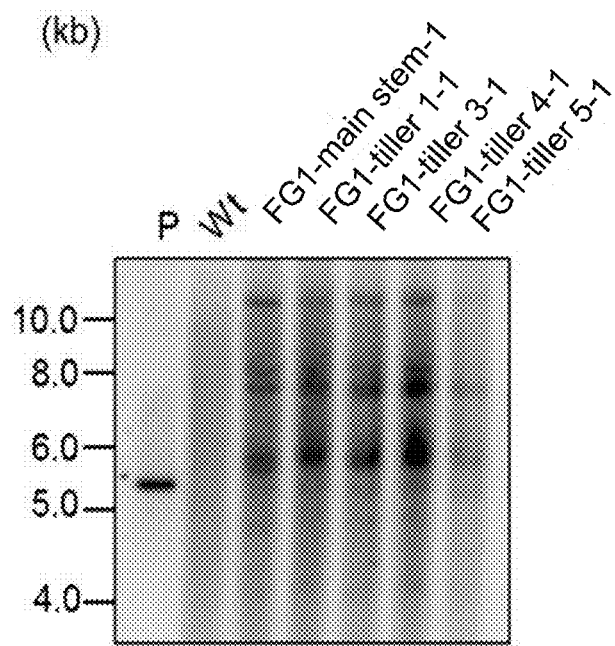
FIG. 5B is a photograph showing the results of Southern analysis of genomic DNAs obtained from young leaves of $T_1$ seeds derived from a main stem and tillers (Example 5).

Next, genomic DNAs obtained from young leaves of fourteen $T_1$ seeds derived from the main stem (FG1-main stem-1 to 14) were treated with HindIII, and Southern blotting analysis was performed with a probe of the GFP gene region. As a result, the same signal pattern was obtained for all the individuals (FIG. 5A). Furthermore, genomic DNAs obtained from young leaves of $T_1$ seeds derived from the main stem and tillers 1, 3, 4, and 5 (FG1-main stem-1, FG1-tiller 1-1, FG1-tiller 3-1, FG1-tiller 4-1, FG1-tiller 5-1) were treated with HindIII, and Southern blotting analysis was performed as described above. As a result, the same signal pattern was obtained for all the individuals (FIG. 5B). It was found from these results that the plurality of $T_1$ seeds obtained from a certain single line of the transgenic individual ($T_0$ generation) had the same genetic information. This suggests that a very small number of shoot apical stem cells transit to a germ cell line, and it was found that a gene can be introduced into the very small number of shoot apical stem cells by the method.

Example 6: Obtainment of Transformant of Corn

In order to confirm whether or not a transformant of corn can be obtained using the same method as the method used to obtain a transformant of wheat, the presence or absence of GFP fluorescence in a shoot apex that had been subjected to a gene introduction process was examined.

1. Study Using Transient Expression System of GFP Fluorescent Protein as Index (1) Preparation of Fully Mature Seed of Corn Fully mature seeds of corn (Snowdent Ohka) were immersed in Haiter (with a hypochlorous acid concentration of 6%), shaken at room temperature for 20 minutes, and washed with sterile water in a clean bench. After having been washed, the seeds were placed on Kimtowel or filter paper moistened with sterile water, and incubated at 30° C. for about 36 hours, and then used in the following experiments.

(2) Exposure of Shoot Apex in Embryo of Fully Mature Seed

An endosperm and an excess portion of a scutellum were removed using a sterile knife (or a sterile scalpel) under a stereoscopic microscope. Thereafter, a coleoptile and leaf primordia in the embryonic moiety of each of the above-mentioned germinated seeds were removed using a leading end of a needle (with a diameter of 0.20 mm), and the shoot apex moiety was thus fully exposed. The thus obtained samples were placed on an MS-maltose medium (4.3 g/L MS salt, MS vitamin, 30 g/L maltose, 0.98 g/L MES, 3% PPM (plant preservative mixture, registered trademark; Nacalai Tesque Inc.), 7.0 g/L phytagel, pH 5.8) at 10 samples per plate. The above-mentioned plates was prepared at two plates per treatment group.

(3) Gene Introduction

This was performed in accordance with the method described in Example 1-1-(3).

(4) Study of Transient Expression Efficiency of GFP Protein

Figure 6:
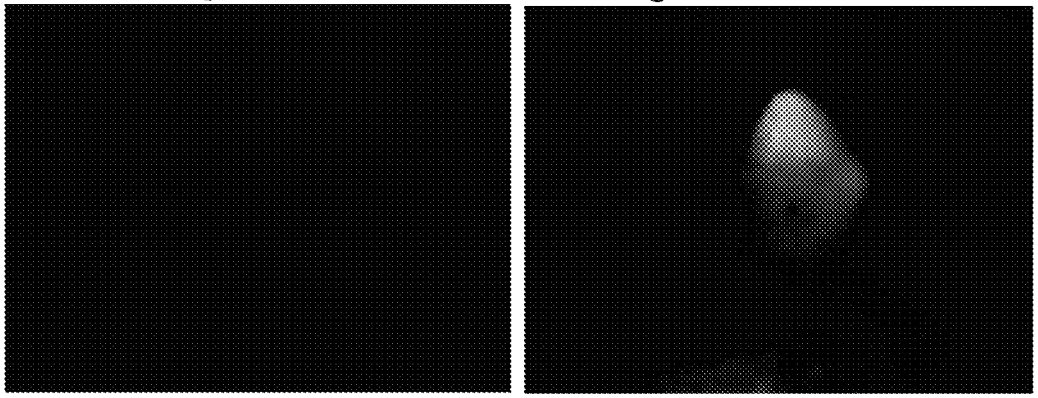
FIG. 6 is a photograph showing a transient expression of GFP in corn (Example 6).

The transfer efficiency of the GFP gene in the shoot apex was calculated by observing GFP fluorescence (excitation: 470/40, absorption: 525/50) absorption: 52/50) in the shoot apex under a stereoscopic fluorescence microscope (MZFL III manufactured by Leica) (FIG. 6). Out of the fully mature embryos subjected to the transformation process, that having 5 or more spots of GFP fluorescence observed in the shoot apex tissue was taken as a transgenic individual, and the gene transfer efficiency was calculated (number of transgenic individuals/number of processed fully mature embryos×100). As a result, the gene transfer efficiencies in the shoot apex in the cases of the gold particles with diameters of 0.8 μm, 0.6 μm, and 0.3 μm were higher than those in the cases of the gold particles with diameters of 1.6 μm and 1.0 μm (Table 6). In particular, when the gold particles with a diameter of 0.6 μm were used, the gene transfer efficiency in the shoot apex was 85%, which was the highest compared with those in the cases of the gold particles with different diameters (Table 6).

TABLE 6

| | Gold particle diameter (μm) | | | | |
|---|---|---|---|---|---|
| | 0.3 | 0.6 | 0.8 | 1.0 | 1.6 |
| Gene transfer efficiency | 25.0% | 85.0% | 20.0% | 5.0% | 5.0% |

Example 7: Obtainment of Transformant of Soybean

In order to confirm whether or not a transformant of soybean can be obtained using the same method as the method used to obtain a transformant of wheat, the presence or absence of GFP fluorescence in a shoot apex that had been subjected to a gene introduction process and the subsequently transformant obtaining efficiency were examined.

1. Study Using Transient Expression System of GFP Fluorescent Protein as Index (1) Preparation of Fully Mature Seed of Soybean Fully mature seeds of soybean (Yukihomare) were immersed in Haiter (with a hypochlorous acid concentration of 6%), shaken at room temperature for 3 minutes, and washed with sterile water in a clean bench. After having been washed, the seeds were placed on Kimtowel or filter paper moistened with sterile water, incubated at 23° C. for about 40 hours, and then used in the following experiments.

(2) Exposure of Shoot Apex in Embryo of Fully Mature Seed

The entire cotyledon was cut out using a sterile knife (or a sterile scalpel) under a stereoscopic microscope, and only a hypocotyl was left. Thereafter, a primary leaf and a base of the hypocotyl were removed using a leading end of a needle (with a diameter of 0.20 mm), and the shoot apex moiety was thus fully exposed. The thus obtained samples were placed on a BM medium (4.3 g/L MS salt, MS vitamin, 3% sucrose, 0.50 g/L MES, 3% PPM (plant preservative mixture; Nacalai Tesque Inc.), 6.0 g/L phytagel, pH 5.7) at about 15 samples per plate.

(3) Gene Introduction

This was performed in accordance with the method described in Example 1-1-(3), proviso that a 35S promoter of a cauliflower mosaic virus (CaMV) was used as a promoter.

(4) Study of Transient Expression Efficiency of GFP Protein

Figure 7:
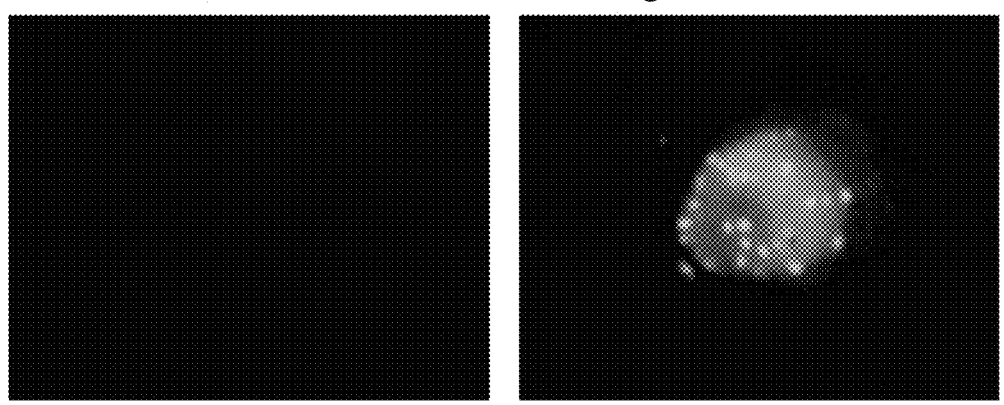
FIG. 7 is a photograph showing a transient expression of GFP in soybean (Example 7).

The transfer efficiency of the GFP gene in the shoot apex was calculated by observing GFP fluorescence (excitation: 470/40, absorption: 525/50) in the shoot apex under a stereoscopic fluorescence microscope (MZFL III manufactured by Leica) (FIG. 7). Out of the fully mature embryo subjected to the transformation process, that having 5 or more spots of GFP fluorescence observed in the shoot apex tissue was taken as a transgenic individual, and the gene transfer efficiency was calculated (number of transgenic individuals/number of processed fully mature embryos× 100). As a result, the gene transfer efficiency in the shoot apex in the case of the gold particles with a diameter of 0.6 μm was 85.0%, which was higher than those in the cases of the gold particles with diameters of 1.6 μm and 1.0 μm (Table 7).

TABLE 7

| | Gold particle diameter (μm) | | |
|---|---|---|---|
| | 0.6 | 1.0 | 1.6 |
| Gene transfer efficiency | 85.0% | 30.6% | 4.3% |

2. Study of $T_0$ Generation Plant Using Genomic PCR as Index (1) Growth of Individual Subjected to Transformation Process An individual that had been subjected to the transformation process was left to stand overnight, and was transferred to a disposable container for plant cell culture (Sigma) in which an RM medium (4.3 g/L MS salt, MS vitamin, 3% sucrose, 0.50 g/L MES, 3% PPM (plant preservative mixture; Nacalai Tesque Inc.), 0.3% Gelrite, pH 5.7) was placed, and was grown in an incubator (23° C., day length of 16 hours). The individual was transferred to a cell tray in which seedling compost for gardening was placed at a time point when the growth of a root and the differentiation of the shoot apex into a leaf were observed. Thereafter, the individual was grown in the same incubator until the second leaf was out.

(2) Presence or Absence of Transgene in Leaf of $T_0$ Plant

In the obtained plant body, the presence or absence of the GFP gene, which is a fluorescence reporter gene was examined using a PCR method. A genomic DNA was extracted from the second leaf (50 mg) using a benzyl chloride method, and PCR reaction was performed using the genomic DNA as a template with primers produced based on the sequences specific to the GFP gene.

```
The sequence of the primer:
                              (SEQ ID NO: 1)
ACGGCCACAAGTTCAGCGT The sequence of the primer:
                              (SEQ ID NO: 2)
ACCATGTGATCGCGCTTCT
```

A PCR reaction mixture was prepared by mixing 20 ng of the genomic DNA 0.25 U of ExTaqHS (TaKaRa), 1.5 µL of accompanying 10×buffer, 2 mM dNTPs, and the pair of primers (each 2.5 pmol) with sterile distilled water such that the total volume was 15 µl.

In the PCR reaction, the PCR reaction mixture was treated at 95° C. for 3 minutes, and subjected to 32 cycles of reaction of 95° C. for 30 seconds, 60° C. for 30 seconds, and 72° C. for 1 minute using TaKaRa PCR Thermal Cycler Dice. After the PCR reaction, electrophoresis was performed on 1.0% agarose gel, and the PCR product was detected through ethidium bromide staining and irradiation with ultraviolet rays. The individual in which an expected 601-bp GFP gene fragment was detected was determined as a transgenic individual.

Regarding the gold particles with a diameter of 0.6 µm used for the gene introduction, the number of the transgenic individuals was determined and used to calculate the gene transfer efficiency with respect to the number of the fully mature embryos subjected to the gene introduction process (number of transgenic individuals/number of processed fully mature embryos×100).

As a result, when the gold particles with a diameter of 0.6 µm were used, the transgene-detected individuals ($T_0$ generation) were 63 individuals out of 470 processed fully mature embryos (the gene transfer efficiency of 13.4%). Therefore, it was found that the transgenic individuals of soybean could be obtained with high efficiency by use of the gold particles with a diameter of 0.6 µm, which had high transient expression efficiency in Example 7-1-(4).

Example 8: Obtainment of Transformant of Barley

In order to confirm whether or not a transformant of barley can be obtained using the same method as the method used to obtain a transformant of wheat, the presence or absence of GFP fluorescence in a shoot apex that had been subjected to a gene introduction process was examined.

1. Study Using Transient Expression System of GFP Fluorescent Protein as Index (1) Preparation of Fully Mature Seed of Barley Fully mature seeds of barley (Wasedori-nijo) were immersed in Haiter (with a hypochlorous acid concentration of 6%), shaken at room temperature for 20 minutes, and washed with sterile water in a clean bench. After having been washed, the seeds were placed on Kimtowel or filter paper moistened with sterile water, and incubated at 4° C. for 2 days. Thereafter, the seeds were incubated at 22° C. for 6 to 12 hours and then used in the following experiments.

(2) Exposure of Shoot Apex in Embryo of Fully Mature Seed

An endosperm and an excess portion of a scutellum were removed using a sterile scalpel under a stereoscopic microscope. Thereafter, a coleoptile and leaf primordia in the embryonic moiety of each of the above-mentioned germinated seeds were removed using a leading end of a needle (with a diameter of 0.20 mm), and the shoot apex moiety was thus fully exposed. The thus obtained samples were placed on an MS-maltose medium (4.3 g/L MS salt, MS vitamin. 30 g/L maltose, 0.98 g/L MES, 3% PPM (plant preservative mixture, registered trademark; Nacalai Tesque Inc.), 7.0 g/L phytagel, pH 5.8) at 30 samples per plate.

(3) Gene Introduction

This was performed in accordance with the method described in Example 1-1-(3).

(4) Study of Transient Expression Efficiency of GFP Protein

Figure 8:
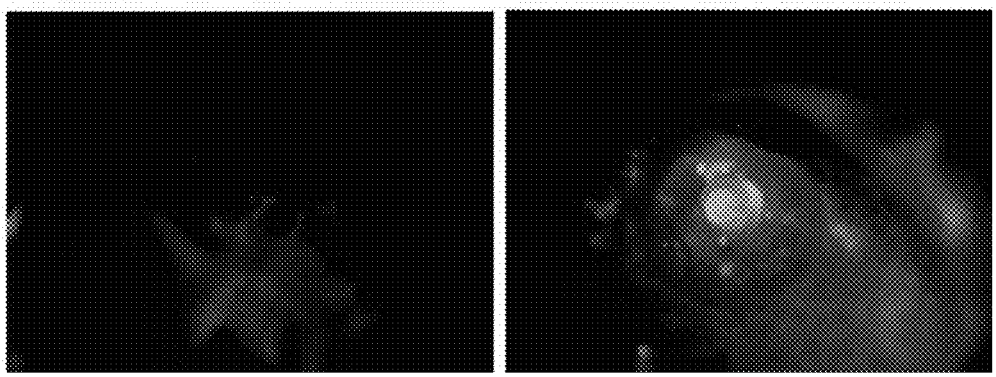
FIG. 8 is a photograph showing a transient expression of GFP in barley (Example 8).

This was performed in accordance with the method described in Example 1-1-(4). As a result, the gene transfer efficiencies in the shoot apex in the cases of the gold particles with diameters of 0.8 µm, 0.6 µm, and 0.3 µm were higher than those in the cases of the gold particles with diameters of 1.6 µm and 1.0 µm (Table 8). In particular, when the gold particles with a diameter of 0.3 µm were used, the gene transfer efficiency in the shoot apex was 80.0%, which was the highest compared with those in the cases of the gold particles with different diameters (FIG. 8, Table 8).

TABLE 8

| | Gold particle diameter (µm) | | | | |
|---|---|---|---|---|---|
| | 0.3 | 0.6 | 0.8 | 1.0 | 1.6 |
| Gene transfer efficiency | 80.0% | 73.3% | 73.3% | 16.7% | 6.7% |

Example 9: Obtainment of Transformant of Potato

In order to confirm whether or not a transformant of potato can be obtained using the same method as the method used to obtain a transformant of wheat, the presence or absence of GFP fluorescence in a shoot apex that had been subjected to a gene introduction process was examined.

1. Study Using Transient Expression System of GFP Fluorescent Protein as Index (1) Preparation of Potato A seed potato (Danshaku) was sterilized using Haiter (with a hypochlorous acid concentration of 1%), washed with water, dried, and was incubated under a fluorescent lamp at 22° C. for 1 to 2 weeks so as to sprout.

(2) Exposure of Shoot Apex

Leaf primordia were removed from a sprout using a sterile scalpel and a leading end of a needle (with a diameter of 0.20 mm) under a stereoscopic microscope, and the shoot apex moiety was thus fully exposed. The thus obtained samples were placed on an MS medium (4.3 g/L MS salt, MS vitamin, 30 g/L sucrose, 0.98 g/L MES, 3% PPM (plant preservative mixture, registered trademark; Nacalai Tesque Inc.), 7.0 g/L phytagel, pH 5.8) at 40 samples per plate.

(3) Gene Introduction

This was performed in accordance with the method described in Example 1-1-(3), proviso that pUC18-35S-GFP was used as an introduction vector.

(4) Study of Transient Expression Efficiency of GFP Protein

Figure 9:
FIG. 9 is a photograph showing a transient expression of GFP in potato (Example 9).

This was performed in accordance with the method described in Example 1-1-(4). As a result. GFP fluorescence could be observed in the shoot apex in the case where the gold particles with a diameter of 0.6 μm were used. (FIG. 9).

Example 10: Transformation Using Linear Plasmid

In order to improve the transformation efficiency the presence or absence of GFP fluorescence in a shoot apex that had been subjected to a gene introduction process by use of a linear plasmid, and the subsequently transformant obtaining efficiency were examined.

1. Study of to Plant Using Genomic PCR as Index (1) Preparation of Fully Mature Seed of Wheat This was performed in accordance with the method described in Example 1-1-(1).

(2) Exposure of Shoot Apex in Embryo of Fully Mature Seed

This was performed in accordance with the method described in Example 1-1-(2).

(3) Preparation of Linear Vector

PCR reaction was performed using the GFP vector (SEQ ID NO: 3) used in Example 1-1-(3) as a template with primers produced based on the sequences (SEQ ID NOs: 4 and 5) specific to a ubiquitin promoter and Nos terminator, respectively or the sequences (SEQ ID NOs: 6 and 7) specific to the vector. Thereafter, the PCR product was purified through ethanol precipitation, and linear vector 1 (Pubi-GFP-Tnos fragment) and linear vector 2 (Pubi-GFP-Tnos fragment-additional 1 kb) was thus produced. In-linear vector 2, about 1.2 kbp and 0.8 kbp of GFP vector-derived sequences were added to the 5' terminus and the 3 terminus of linear vector 1, respectively.

```
The sequence of the primer:
                            (SEQ ID NO: 4)
CGACGGCCAGTGCCAAGCTT The sequence of the primer:
                            (SEQ ID NO: 5)
ATGACCATGATTACGAATTC The sequence of the primer:
                            (SEQ ID NO: 6)
AAGCTAGAGTAAGTAGTTCGCCA The sequence of the primer:
                            (SEQ ID NO: 7)
ATACTGTCCTTCTAGTGTAGCCG
```

APCR reaction mixture was prepared by mixing 10 ng of the vector DNA, 1.0 U of PrimeSTAR (registered trademark) GXL DNA Polymerase (TaKaRa), 4.0 μL of accompanying 5×buffer, 0.2 mM dNTPs, and the pair of primers (each 2.5 pmol) with sterile distilled water such that the total volume was 20 μl.

In the PCR reaction, the PCR reaction mixture was subjected to 40 cycles of reaction of 98° C. for 10 seconds, 60° C. for 15 seconds, and 68° C. for 2 minutes and 30 seconds using ThKaRa PCR Thermal Cycler Dice. The PCR product was purified through ethanol precipitation, and dissolved in sterile water such that the concentration was 1 μg/μL. The obtained solution was used in the following experiments.

(4) Gene Introduction

This was performed in accordance with the method described in Example 1-1-(3), proviso that the gold particles with a diameter of 0.6 μm were used, and the GFP vector solution or the linear vector solution (1 μg/μL) was added such that the amount of the vector was 10 μg per 750 μg of the gold particles.

(5) Growth of Individual Subjected to Transformation Process

An individual that had been subjected to the transformation process was left to stand overnight, and was transferred to a disposable container for plant cell culture (Sigma) in which an MS-maltose medium was placed, and was grown in a long-day condition (22° C., day length of 16 hours). After grown for 3 to 4 weeks, the individual was transferred to a pot in which seedling compost for gardening was placed at a time point when second and third leaves were observed. Thereafter, the individual was grown in a long-day condition in a climatic chamber (24° C., day length of 16 hours, humidity of 50 to 70%) until fourth to sixth leaves were out.

(6) Presence or Absence of Transgene in Leaf of $T_0$ Plant

This was performed in accordance with the method described in Example 1-2-(5). The respective vector was used in the transformation process, and the obtained transgene-detected individuals ($T_0$ generation) was determined and used to calculate the gene transfer efficiency with respect to the number of the fully mature embryos subjected to the gene introduction process (number of transgenic individuals/number of processed fully mature embryos× 100). As a result, when the linear vector 1 and linear vector 2 were used in the experiments, the gene transfer efficiencies were 7.1% and 14.2%, respectively (Table 9), compared with the gene transfer efficiency (4.2%) with the conventional GFP vector for introduction. The gene transfer efficiency was particularly high with linear vector 2. It was found from these results that a linear vector (nucleic acid cassette to be introduced) may be preferable for gene introduction, and use of a linear vector having respective nucleic acids of 0.8 kb or more added to the two termini of a nucleic acid cassette to be introduced, respectively may be more preferable.

TABLE 9

| Introduction vector form | Introduction vector length (bp) | No. of processed individuals | Transgenic individuals ($T_0$ generation) | Gene transfer efficiency ($T_0$ generation) |
|---|---|---|---|---|
| Circular (GFP vector) | 5,646 | 30 | 2 | |
| | | 30 | 1 | |
| | | 30 | 1 | |
| | | 30 | 1 | |
| Total | | 120 | 5 | 4.2% |
| Linear vector 1 | 3,045 | 30 | 0 | |
| | | 30 | 4 | |
| | | 34 | 4 | |
| | | 33 | 1 | |
| Total | | 127 | 9 | 7.1% |
| Linear vector 2 | 5,076 | 30 | 6 | |
| | | 30 | 4 | |
| | | 30 | 3 | |
| | | 30 | 4 | |
| Total | | 120 | 17 | 14.2% |

Example 11: Obtainment of Transformant of Rice

A transformant of rice can also be obtained using substantially the same method as the method used to obtain a transformant of wheat.

1. Preparation of Fully Mature Seed of Rice

After threshed fully mature seeds of rice (strain: Nihonbare) are sterilized and washed in accordance with the method described in Example 1-1-(1), the seeds are placed on Kimtowel or filter paper moistened with sterile water, incubated at 25° C. for about 24 to 48 hours, and then used in the following experiments.

2. Exposure of Shoot Apex in Embryo of Fully Mature Seed

A shoot apex of an embryo in the fully mature seed is fully exposed in accordance with the method described in Example 1-1-(2). The fully mature embryos including an exposed shoot apex are placed on an MS-maltose medium at about thirty embryos per plate.

3. Gene Introduction

The gene introduction into the shoot apex of the fully mature embryo of rice is performed in accordance with the method described in Example 1-1-(3).

4. Selection Using Transient Expression of GFP Protein as Index

Out of the individuals subjected to the transformation process using the gold particles with a diameter of 0.6 μm, an individual having 5 or more spots of GFP fluorescence observed in the shoot apex tissue is selected in accordance with the method described in Example 1-1-(4).

5. Growth of Individual Subjected to Transformation Process

The individual subjected to the transformation process is grown in accordance with the method described in Example 1-2-(4).

6. Confirmation of Transgene in Leaf of $T_0$ Plant

A transgene-detected individual is obtained in accordance with the method described in Example 1-2-(5). The obtained individual is grown, and seeds of next generation are obtained, thus making it possible to produce a stable transformant.

Example 12: Obtainment of Transformant of Apple

A transformant of apple can also be obtained using substantially the same method as the method used to obtain a transformant of wheat.

1. Preparation of Shoot Apex of Apple

The preparation of a shoot apex of apple (strain: Jonagold) is performed according to the induction conditions for shoot apex culture described in Plant Tissue Culture Letters, 9(2), 69-73 (1992).

2. Exposure of Shoot Apex

The shoot apexes prepared using the method in 1, are placed on an MS-maltose medium (4.3 g/L MS salt, MS vitamin, 30 g/L maltose, 0.98 g/L MES, 3% PPM (plant preservative mixture, registered trademark; Nacalai Tesque Inc.), 7.0 g/L phytagel, pH 5.8) at about thirty apexes per plate.

3. Gene Introduction

This is performed in accordance with the method described in Example 1-1-(3), proviso that a 35S promoter of a cauliflower mosaic virus (CaMV) is used as a promoter.

4. Selection Using Transient Expression of GFP Protein as Index

Out of the individuals subjected to the transformation process using the gold particles with a diameter of 0.6 μm, an individual having 5 or more spots of GFP fluorescence observed in the shoot apex tissue is selected in accordance with the method described in Example 1-1-(4).

5. Growth of Individual Subjected to Transformation Process

The individual subjected to the transformation process is grown in accordance with the method described in Example 1-2-(4).

6. Confirmation of Transgene in Leaf of to Plant

An transgene-detected individual is obtained in accordance with the method described in Example 1-2-(5). The obtained individual is grown, and seeds of next generation are obtained, thus making it possible to produce a stable transformant.

One or more embodiments of the present invention can be applied to the agricultural industry, pharmaceutical industry, and enzyme industry.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

LIST OF REFERENCE NUMERALS

Al Aleurone layer
E Endosperm

---

What is claimed is:

1. A method for transforming a plant, comprising:
   coating a microparticle having a diameter in a range from 0.3 to 0.8 μm with at least one nucleic acid;
   selecting the plant from the group consisting of wheat, barley, rice, corn, soybean, potato, and apple;
   exposing a shoot apex of the plant by removing tissues, wherein the shoot apex is selected from the group consisting of a shoot apex of an embryo of a fully mature seed, a shoot apex of a young bud of a tuber, and a shoot apex of a terminal bud or a lateral bud, wherein the tissues removed in the exposing the shoot apex are:
   (i) for the embryo of the fully mature seed, an endosperm, a coleoptile, a leaf primordium, and an excess of a scutellum of the fully mature seed;
   (ii) for the young bud of the tuber, the tuber and a leaf primordium of the young bud of the tuber; and
   (iii) for the terminal bud or the lateral bud, a leaf primordium of the shoot apex of the terminal bud or of the lateral bud;
   bombarding the exposed shoot apex of the plant with the coated microparticle using a gene gun, wherein in the bombarding,
      a stopping plate is set on the gene gun so that a distance between the stopping plate and the shoot apex is in a range of 6 cm or less,
      the microparticle is bombarded at a gas pressure from 1,100 to 1,600 psi,
      a number of shots for bombarding the shoot apex of the plant with the coated microparticle is two or more, and
      an L2 layer cell in the shoot apex is bombarded with the coated microparticle,
         wherein, among the L2 layer cell in the shoot apex, a shoot apical stem cell that differentiates into a germ cell line is bombarded with the coated microparticle;
   growing the shoot apex bombarded with the coated microparticle so as to obtain a plant body; and
   selecting a transformed plant body from the plant body; wherein the selecting does not depend on the expression of a protein encoded by a selective marker gene.

2. The method according to claim 1, wherein the growing the shoot apex bombarded with the coated microparticle is performed on a medium free from antibiotics.

3. The method according to claim 1, wherein the growing the shoot apex bombarded with the coated microparticle is performed on a medium free from plant hormones.

4. The method according to claim 1, wherein the growing the shoot apex bombarded with the coated microparticle is performed on a medium free from antibiotics and plant hormones.

5. The method according to claim 1, wherein the shoot apex of the plant is the shoot apex of the embryo of the fully mature seed.

6. The method according to claim 1, wherein the shoot apex of the plant is the shoot apex of the young bud of the tuber.

7. The method according to claim 1, wherein the shoot apex of the plant is the shoot apex of the terminal bud or the lateral bud.

8. The method according to claim 1, wherein the at least one nucleic acid is a linear DNA comprising a nucleic acid cassette to be introduced.

9. The method according to claim 8, wherein the linear DNA is a linear plasmid and further comprises 0.8 to 1.2 kb-long nucleic acids located at each terminus of the nucleic acid cassette.

10. The method according to claim 1, wherein the fully mature seed is a fully mature seed comprising a root having a length of 1 mm or less.

11. The method according to claim 1, further comprising producing a transformant of the plant by growing the transformed plant body.

12. The method according to claim 1, wherein the selective marker gene is at least one gene selected from the group consisting of herbicide resistance genes, drug resistance genes, and fluorescence or luminescence reporter genes.

13. The method according to claim 1, wherein the plant is selected from the group consisting of wheat, barley, corn, and soybean.

14. The method according to claim 1, wherein the microparticle has a diameter in a range from 0.3 to 0.7 μm.

* * * * *